US011253518B2

(12) United States Patent
Wurst

(10) Patent No.: US 11,253,518 B2
(45) Date of Patent: Feb. 22, 2022

(54) METHODS AND COMPOSITIONS FOR THE TREATMENT OF HAIR LOSS

(71) Applicant: Aneira Pharma, Inc., San Diego, CA (US)

(72) Inventor: John Edward Wurst, Poway, CA (US)

(73) Assignee: Aneira Pharma, Inc., San Diego, CA (US)

( * ) Notice: Subject to any disclaimer, the term of this patent is extended or adjusted under 35 U.S.C. 154(b) by 0 days.

(21) Appl. No.: 16/983,870

(22) Filed: Aug. 3, 2020

(65) Prior Publication Data

US 2021/0038683 A1 Feb. 11, 2021

Related U.S. Application Data

(60) Provisional application No. 63/100,611, filed on Mar. 23, 2020, provisional application No. 62/895,869, filed on Sep. 4, 2019, provisional application No. 62/883,809, filed on Aug. 7, 2019.

(51) Int. Cl.

| A61K 31/506 | (2006.01) |
|---|---|
| A61P 17/14 | (2006.01) |
| A61K 31/222 | (2006.01) |
| A61K 47/10 | (2017.01) |
| A61K 47/12 | (2006.01) |
| A61K 47/26 | (2006.01) |
| A61K 31/25 | (2006.01) |
| A61K 38/13 | (2006.01) |
| A61K 31/5575 | (2006.01) |

(52) U.S. Cl.
CPC .......... *A61K 31/506* (2013.01); *A61K 31/222* (2013.01); *A61K 31/25* (2013.01); *A61K 31/5575* (2013.01); *A61K 38/13* (2013.01); *A61K 47/10* (2013.01); *A61K 47/12* (2013.01); *A61K 47/26* (2013.01); *A61P 17/14* (2018.01)

(58) Field of Classification Search
None
See application file for complete search history.

(56) References Cited

U.S. PATENT DOCUMENTS

| 4,596,812 A | 6/1986 | Chidsey et al. |
|---|---|---|
| 4,820,512 A | 4/1989 | Grollier |
| 4,828,837 A | 5/1989 | Uster et al. |
| 5,030,442 A | 7/1991 | Uster et al. |
| 5,225,189 A | 7/1993 | Pena |
| 5,407,944 A | 4/1995 | Goldman |
| 5,620,980 A | 4/1997 | Samour |
| 5,834,014 A | 11/1998 | Weiner et al. |
| 6,262,105 B1 | 7/2001 | Johnstone |
| 6,403,649 B1 | 6/2002 | Woodward et al. |
| 6,465,514 B1 | 10/2002 | Hallam et al. |
| 6,596,266 B2 | 7/2003 | Catalfo et al. |
| 6,946,120 B2 | 9/2005 | Wai-Chiu et al. |
| 7,388,029 B2 | 6/2008 | Delong et al. |
| 7,442,369 B1 | 10/2008 | Pena et al. |
| 7,749,489 B2 | 7/2010 | Malek |
| 7,803,357 B2 | 9/2010 | Cappello |
| 8,038,988 B2 | 10/2011 | Woodward et al. |
| 8,293,789 B2 | 10/2012 | Jimenez-Bayardo et al. |
| 8,758,733 B2 | 6/2014 | Ahluwalia et al. |
| 8,906,962 B2 | 12/2014 | Delong et al. |
| 9,138,480 B2 | 9/2015 | Trogden et al. |
| 9,149,484 B2 | 10/2015 | Warner et al. |
| 9,226,931 B2 | 1/2016 | Ahluwalia et al. |
| 9,700,503 B2 | 7/2017 | Woodward et al. |
| 9,750,750 B2 | 9/2017 | Trogden et al. |
| 9,763,359 B2 | 9/2017 | Chan |
| 9,849,140 B2 | 12/2017 | Warner et al. |
| 10,188,661 B2 | 1/2019 | Singer et al. |
| 10,470,992 B2 | 11/2019 | Sekhavat |
| 2004/0082660 A1 | 4/2004 | Ueno |
| 2004/0115234 A1 | 6/2004 | Gewirtz |
| 2005/0079139 A1 | 4/2005 | Jacques et al. |
| 2007/0160562 A1 | 7/2007 | Brinkenhoff |
| 2008/0206156 A1 | 8/2008 | Cronk |
| 2010/0204335 A1 | 8/2010 | Beddingfield et al. |
| 2010/0210720 A1 | 8/2010 | Pilotaz et al. |
| 2012/0129789 A1 | 5/2012 | Yoelin |
| 2013/0041025 A1 | 2/2013 | Walt et al. |
| 2014/0322148 A1* | 10/2014 | Jackson ................ A61Q 7/00 424/59 |
| 2015/0072963 A1 | 3/2015 | Cotsarelis et al. |
| 2015/0164765 A1* | 6/2015 | Yoelin ................... A61K 8/42 514/20.5 |
| 2016/0136071 A1 | 5/2016 | Corby, Jr. |
| 2016/0213590 A1* | 7/2016 | Sekhavat ........... A61K 31/5575 |

(Continued)

FOREIGN PATENT DOCUMENTS

| CA | 2309373 A1 | 11/2000 |
|---|---|---|
| EP | 3494955 A1 | 6/2019 |
| JP | 2003155218 A | 5/2003 |

(Continued)

OTHER PUBLICATIONS

Aditya Gupta, et al., Efficacy of Off-Label Treatments for the Management of Androgenetic Alopecia: A Review, Clinical Drug Investigation, Jan. 2019, 8 pages.
Ulrike Blume-Peytavi, et al., A randomized double-blind placebo-controlled pilot study to assess the efficacy of a 24-week topical treatment by latanoprost 0.1% on hair growth and pigmentation in healthy volunteers with androgenetic alopecia, J Am Acad Dermatol, vol. 66, No. 5, May 2012, pp. 794-800.
Gita Faghihi, et al, The efficacy of latanoprost in the treatment of alopecia areata of eyelashes and eyebrows, Eur J Dermatol, 2009; 19, pp. 586-587.
Justine A. Ellis, et al., Male pattern baldness: current treatments, future prospects, Drug Discovery Today, vol. 13, No. 17/18, Sep. 2008, pp. 791-797.
S. Sasaki, et al., Influence of prostaglandin F2a and its analogues on hair regrowth and follicular melanogenesis in a murine model, Experimental Dermatology, 2005, pp. 323-328.
Hideo Uno et al., Effect of Latanoprost on Hair Growth in the Bald Scalp of the Stump-tailed Macacque: A Pilot Study, Acta Derm Venereol, 2002, pp. 7-12.

(Continued)

*Primary Examiner* — Nannette Holloman

(57) ABSTRACT

Compositions and methods for the treatment of hair growth and the prevention of hair loss.

20 Claims, 5 Drawing Sheets

(56) References Cited

U.S. PATENT DOCUMENTS

| | | | |
|---|---|---|---|
| 2017/0181950 A1 | 6/2017 | Wu | |
| 2018/0200263 A1* | 7/2018 | Grimes | A61K 31/353 |

FOREIGN PATENT DOCUMENTS

| | | |
|---|---|---|
| WO | 2005013928 A1 | 2/2005 |
| WO | 2009151828 A1 | 12/2009 |
| WO | 2011081861 A2 | 7/2011 |
| WO | 2013078259 A2 | 5/2013 |
| WO | 2013106565 A1 | 7/2013 |
| WO | 2019034571 A1 | 2/2019 |

OTHER PUBLICATIONS

Paula M. Oliveira, et al., LC-MS bioanalytical method for simultaneous determination of latanoprost and minoxidil in the skin, Journal of Pharmaceutical and Biomedical Analysis, Mar. 6, 2020, 26 pages.

Coleman, H., The Cosmetic Effects of Bimatoprost vs. Latanoprost vs. Travoprost vs. Placebo on Eyelash Growth. American Academy of Optometry, 2010, 3 pages.

Jorge Ocampo-Garza, et al., New drugs under investigation for the treatment of alopecias, Expert Opinion on Investigational Drugs, ISSN 1354-3784, Jan. 15, 2019, 34 pages.

Murad, et al, Treatment for facial alopecia areata: A systematic review with evidence-based analysis, Journal of American Dermatology, Apr. 14, 2017, 10 pages.

Amal Ahmad El-Ashmawy, et al, Efficacy of topical latanoprost versus minoxidil and betamethasone valerate on the treatment of alopecia areata, Journal of Dermatological Treatment, vol. 29, No. 1, Jun. 15, 2017, pp. 55-64.

Ozyurt S., et al, Hypertrichosis ofthemalar areas andpoliosisofthe eyelashes causedby latanoprost, Actas Dermosifiliogr, 2015, pp. 74-75.

Lauren L. Levy, et al, Female pattern alopecia: current perspectives, International Journal of Women's Health, Aug. 28, 2013, pp. 541-556.

Im Coronel-Perez, et al, Latanoprost in the treatment of eyelash alopecia in alopecia areata universalis, DJEADV, 2010, No. 24, pp. 481-485.

Rajarshi Mukhopadhyay, et al, A rare complication from prostaglandin analogue therapy, Clinical and Experimental Optometry, 2009, 92:2, pp. 137-138.

Karzan G. Khidir, et al, The prostamide-related glaucoma therapy, bimatoprost, offers a novel approach for treating scalp alopecias, The FASEB Journal, 27 (2), Feb. 2013, pp. 557-567.

Y. Liang, et al, Identification and pharmacological characterization of the prostaglandin FP receptor and FP receptor variat complexes, British Journal of Pharmacology, 2008, pp. 1079-1093.

PFIZER Manufacturing Belgium NV, Xalatan Package Insert for the 2.5 mL fill—Package of 1 Bottle, Aug. 2011, 14 pages.

T. Ogiso, et al. Transfollicular Drug Delivery: Penetration of Drugs Through Human Scalp Skin and Comparison of Penetration Between Scalp and Abdominal Skins In Vitro, Journal of Drug Targeting, 2002, vol. 10 (5), pp. 369-378.

Clinical Investigation, A Prospective Study of Iridial Pigmentation and Eyelash Changes Due to Ophthalmic Treatment with Latanoprost, Japanese Journal of Ophthalmology, Mar. 2004, vol. 48, Issue 2, pp. 141-147 (first online Feb. 10, 2016).

Sardesai et al, A Study to Evaluate the Efficacy of Various Topical Treatment Modalities for Alopecia Areata, International Journal of Trichology, 2012, Oct.-Dec. 4 (4), pp. 265-270.

Garg et al, Alpoecia areata: edivence-based treatments, Semin Cutan Med Sug., Mar. 2009, one page.

Schweiger et al., Topical Bimatoprost for the Treatment of Eyebrow Hypotrichosis, Journal of Drugs in Dermatology, vol. II, Issue I, Jan. 2012, 106-108.

Hawkshaw et al., Identifying novel strategies for treating human hair loss disorders: Cyclosporine A suppresses the Wnt inhibitor, SFRP1, in the dermal papilla of human scalp hair follicles, PLOS Biology Fifteenth Anniversary, May 8, 2018, 12 pages.

Edited by Rowe et al., (2009), "Handbook of Pharmaceutical Excipients (6th ed.)", London: APhA, (PhP) Pharmaceutical Press., pp. 468-470. (Year: 2009).

National Center for Biotechnology Information. "PubChem Compound Summary for CID 8146, Diethylene glycol monoethyl ether" PubChem, https://pubchem.ncbi.nlm.nih.gov/compound/Diethylene-glycol-monoethyl-ether. Created Mar. 26, 2005. Accessed Jan. 16, 2021. (Year: 2005).

Bloch et al., Latanoprost and minoxidil: Comparative double-blind, placebo-controlled study for the treatment of hair loss, Surg Cosmet Dermatol. Rio de Janeiro v.10 n.1 Jan.-Mar. 2018 p. 39-43, DOI: http://dx.doi.org/10.5935/scd1984-8773.20181011015, 2018.

Fiedler-Weiss, Topical minoxidil solution (1% and 5%) in the treatment of alopecia areata, Journal of American Academy of Dermatology, vol. 16, No. 3, part 2, pp. 745-748, Mar. 1987.

Johnstone et al., Prostaglandin-Induced Hair Growth, Survey of Ophthalmology, vol. 47, supplement 1, Aug. 2002.

Patel et al., Bioanalytical Method Development and Validation for Latanoprost Quantification in Pharmaceutical Opthalmic Microemulsion Formulation by RP-HPLC, Journal of Analytical & Bioanalytical Techniques, vol. 6, issue 6, 1000284, 2015.

Ahmed Abduthussein Kawen,Topical Minoxidil alone and with Lanoprost in Localizad Alopecia Areata Treatment Comparative Study (2019-2020), Systematic Review Pharmacy, vol. 11, Issue 4, pp. 164-169, 2020.

* cited by examiner

METHODS AND COMPOSITIONS FOR THE TREATMENT OF HAIR LOSS

CROSS-REFERENCE TO RELATED APPLICATIONS

This application claims priority to the benefit of U.S. Provisional Patent Application Ser. No. 62/883,809, filed on Aug. 7, 2019 and U.S. Provisional Patent Application Ser. No. 62/895,869, filed on Sep. 4, 2019 and U.S. Provisional patent application Ser. No. 63/100,611, filed on Mar. 23, 2020, the disclosures of which are hereby incorporated by reference in their entireties.

1. FIELD OF THE INVENTION

The present invention is directed to the use of certain prostaglandin analogues alone and in combination with other compounds such as cyclosporine, to prevent hair loss and/or grow hair. The present invention is also directed to formulations containing prostaglandin analogues and cyclosporine to grow hair or prevent hair loss on the scalp and other areas of the body. The present invention is also directed to formulations and methods for treating certain hair loss disorders such as androgenetic alopecia and alopecia areata.

2. BACKGROUND OF THE INVENTION

Hair loss is a psychologically devastating condition causing significant psychological stress in both men and women. Thirty percent of all males will experience some hair loss by the age of thirty years, fifty percent by the age of fifty years, and eighty percent by the age of seventy years. By age sixty, forty percent of women experience hair loss. Negative effects on quality of life due to hair loss have been reported by men and in particular adolescents and women.

Hair growth is generally divided into four phases.

The anagen phase is the phase of active hair growth which lasts two to six years but generally lasts three to five years with scalp hair. During anagen, the epithelial compartment of the hair follicle undergoes rapid proliferation, with the greatest proliferation in the bulb matrix cells and follicles assume bulb anagen morphology. In fact, it is possible to determine which phase a hair is in by studying the follicle bulb morphology. The catagen phase is a short transitional phase between the anagen phase and the telogen phases which lasts seven to fourteen days with scalp hair. The telogen phase is called the "resting phase" where hair growth ceases before the hair is eventually shed and generally lasts four to eight weeks and the dermal papilla fully separates from the hair follicle. A fourth stage, which is either the end of the telogen phase or the beginning of the anagen phase, is the exogen phase where the old hair is shed.

The anagen phase begins again with the dermal papilla moving back up to meet the hair follicle and new hair growth begins again where the new hair ejects the old hair (see FIG. 2).

In humans without a hair loss disorder, about ninety percent of the hairs on the scalp are in the anagen phase, about one to two percent of hairs are in the catagen phase and about eight to nine percent of scalp hair are in the telogen phase. With the onset of androgenetic alopecia, a greater proportion of hair are in the telogen phase and fewer hairs fewer are in the anagen phase. The patient has significantly fewer follicles than people suffering no hair loss disorder, with a typical bald person having roughly three hundred hair follicles per square inch on their scalp while a person with no hair loss disorder will have about four hundred and fifty hair follicles per square inch. Perhaps more importantly, in the active hair follicles in a person suffering from androgenetic alopecia, more of the hairs in the follicles will be vellus hairs rather than terminal hairs which are longer, thicker in diameter and more pigmented. Further, an increased number of hairs will be in the telogen phase.

3. SUMMARY OF THE INVENTION

The Summary of Invention includes the following embodiments:

1. A composition for use in the treatment of hair loss comprising about 0.05%-0.1% w/w, w/v, or v/v latanoprost or latanoprost acid and 0.05%-0.1% w/w, w/v, or v/v cyclosporine A and 1.0%-15.0% w/w, w/v, or v/v diethylene glycol monoethyl ether.
2. The composition of embodiment 1 wherein the composition has about 0.05% w/w, w/v, or v/v latanoprost or latanoprost acid and about 0.06% w/w, w/v, or v/v cyclosporine A and about 10% w/w, w/v, or v/v diethylene glycol monoethyl ether.
3. The composition of embodiment 2 further comprising oleyl alcohol.
4. The composition further comprising polyethylene glycol or propylene glycol.
5. A composition for use in growing hair on a patient experiencing hair loss comprising about 0.05%-0.1% w/w, w/v, or v/v latanoprost or latanoprost acid and 0.05%-0.1% w/w, w/v, or v/v cyclosporine A and 5.0%-15.0% w/w, w/v, or v/v CAPTEX 300 EP/NF.
6. The composition of embodiment 5 wherein composition comprises 0.06% w/w, w/v, or v/v latanoprost or latanoprost acid and 0.08% w/w, w/v, or v/v cyclosporine A.
7. The composition of embodiment 6 further comprising 10% w/w, w/v, or v/v CAPTEX 300 EP/NF.
8. A composition for use in treating hair loss comprising about 0.05%-0.1% w/w, w/v, or v/v travoprost or travoprost acid and 0.05%-0.1% w/w, w/v, or v/v cyclosporine A.
9. The composition according to embodiment 8 further comprising one selected from the group consisting of diethylene glycol monoethyl ether, CAPTEX 300 EP/NF, propylene glycol and polyethylene glycol.
10. The composition according to embodiments 1, 5, 8 and 9 further comprising oleic acid.
11. A method of preventing hair loss on a patient comprising administering a formulation according to one of embodiments 1, 5, 8 and 9 to a patient in need thereof.
12. The method of embodiment 11 wherein the patient is suffering from alopecia areata and the formulation is applied once a day to areas on the scalp experiencing hair loss.
13. The method of embodiment 12 wherein the formulation is applied twice a day.
14. A method for causing hair growth in a patient suffering from hair loss comprising administering a formulation according to one of embodiments 1, 5, 8 and 9 to a patient in need thereof and the method downregulates T cell infiltrates in the area of the follicular bulb.
15. The method of embodiment 14 wherein the patient experiences hair growth to a greater extent by applying the formulation of one of embodiments 1, 5, 8 and 9 as compared to if the patient had not applied the formulation.
16. The method of embodiments 10-15 wherein the formulation maintains the hair in anagen phase longer than if the formulation had not been applied.
17. The method of embodiment 14 wherein the patient reverses a substantial amount of hair loss.
18. The method of embodiment 14 wherein the formulation comprises 0.06% w/w, w/v, or v/v latanoprost acid and 0.08% w/w, w/v, or v/v cyclosporine A and a pharmaceutically acceptable solvent and a penetration enhancer.
19. The method of growing hair on a scalp of a patient wherein the formulation comprises 0.1% w/w, w/v, or v/v latanoprost or latanoprost free acid and cyclosporine.
20. The method of embodiment 19 wherein the cyclosporine is cyclosporine A.
21. A composition for use in the treatment of hair loss comprising about 0.05%-0.1% w/w, w/v, or v/v bimatoprost and 0.05%-0.1% cyclosporine A and 1.0%-25.0% w/w, w/v, or v/v diethylene glycol monoethyl ether.
22. A composition for use in growing hair comprising about 0.05%-0.1% w/w, w/v, or v/v bimatoprost and 0.05%-0.1% cyclosporine A and 1.0%-15.0% w/w, w/v, or v/v diethylene glycol monoethyl ether.
23. A composition for use in the treatment of hair loss or to grow hair comprising about 0.05%-0.5% w/w, w/v, or v/v latanoprost or latanoprost acid and 1.0%-7.0% w/w, w/v, or v/v minoxidil or minoxidil sulphate.
24. The composition of embodiment 23 wherein the composition has about 0.1% or 0.3% w/w, w/v or v/v latanoprost or latanoprost acid and about 5.0% w/w minoxidil or minoxidil sulphate.
25. The composition of embodiment 23 further comprising one selected from the group consisting of oleyl alcohol, ethanol, oleic acid and diethylene glycol monoethyl ether.
26. The composition of embodiment 23 wherein the composition has one selected from the group consisting of 0.1%, 0.2% or 0.3% w/w, w/v, or v/v latanoprost or latanoprost acid and one selected from the group consisting of 4.0%, 5.0%, 6.0% and 7.0% w/w, w/v, or v/v minoxidil or minoxidil sulphate.
27. A composition for use in the treatment of hair loss or to grow hair comprising about 0.05%-0.1% w/w, w/v, or v/v bimatoprost or bimatoprost acid and 1.0%-5.0% w/w, w/v, or v/v minoxidil or minoxidil sulphate.
28. The composition of embodiment 27 wherein the composition has one selected from the one selected form the group consisting of 0.1%, 0.2% and 0.3% w/w, w/v, or v/v bimatoprost and one selected from the group consisting of 4.0%, 5.0%, 6.0% and 7.0% w/w, w/v, or v/v minoxidil.
29. The composition of embodiment 27 further comprising oleyl alcohol, oleic acid or ethanol.
30. The composition of embodiment 27 further comprising propylene glycol or polyethylene glycol.
31. A composition for use in the treatment of hair loss or to grow hair comprising about 0.05%-0.5% w/w, w/v, or v/v travoprost or travoprost free acid and 1.0%-7.0% w/w, w/v, or v/v minoxidil or minoxidil sulphate.
32. The composition of embodiment 31 wherein the composition has about 0.1% w/w, w/v, or v/v travoprost or travoprost free acid and about 5.0% w/w, w/v, or v/v minoxidil or minoxidil sulphate and at least 5% w/w, w/v, or v/v diethylene glycol monoethyl ether.
33. The composition of any of the embodiments 1-10 and 20-32 wherein the composition is applied to the skin beneath the eyebrows of a patient to cause eyebrows to grow.
34. The composition of any of the embodiments 1-10 and 20-32 wherein the composition is applied to the upper or lower eyelid margin of a patient to cause eyelashes to grow.
35. The composition of any of the embodiments 1-32 wherein the composition is applied to the skin beneath the mustache or beard of a patient to cause hairs of the mustache or beard to grow.
36. A method of converting vellus hair to terminal hair by application of the formulation of embodiments 1-10 and 21-32 to the locale of the vellus hair on a patient.
37. A method of converting intermediate hair to terminal hair by application of the formulation of embodiment 23 to the locale of the vellus hair on a patient.
38. A method of increasing at least one selected from length, thickness and pigmentation of hair by the application of a composition of embodiment 1-10 or 21-32 to the scalp of a patient.
39. The composition of embodiment 23, 27, 31 or 33 wherein the composition is a gel.
40. The composition of embodiment 39 wherein the gel is applied to the eyebrows in one selected from the group consisting of once a day, twice a day or three times a day.
41. The composition of embodiment 39 wherein the gel comprises at least one selected from the group consisting of sodium carboxymethyl cellulose, hyaluronic acid or carbodiimide and or mixtures thereof.
42. The composition of embodiment 41 wherein the sodium carboxymethyl cellulose is selected form the group consisting of low viscosity (90,000 Daltons), medium viscosity (250,000 Daltons) and high viscosity (700,000 Daltons) carboxymethyl cellulose and/or mixtures thereof.
43. The composition of embodiments 40 and 41 wherein the gel is applied to the eyebrows once or twice a day.
44. A first composition comprising latanoprost or latanoprost acid and minoxidil or minoxidil sulphate wherein the application of the composition to the skin results in a faster onset of hair growth as compared to either latanoprost or latanoprost acid and minoxidil or minoxidil sulphate applied as monotherapy to the skin and at the same concentration as in the first composition.
45. The composition of embodiment 44 wherein the first composition comprising latanoprost or latanoprost acid and minoxidil are present at the same individual concentrations as latanoprost or latanoprost acid and minoxidil applied alone as monotherapies.
46. The composition of embodiments 44 or 45 wherein the composition is applied to one selected from the group consisting of the scalp, the skin beneath the eyebrows, upper eyelid margin, lower eyelid margin and the face.
47. A first composition comprising latanoprost or latanoprost acid and minoxidil or minoxidil sulphate wherein the application of the first composition to the skin results in greater hair growth as compared to either latanoprost or latanoprost acid and minoxidil or minoxidil sulphate applied to the skin alone as monotherapies at the same individual concentrations as they exist in the first composition.

48. The first composition of embodiment 47 wherein the first composition comprising latanoprost or latanoprost acid and minoxidil or minoxidil sulphate when applied to the scalp, the skin beneath the eyebrows, upper eyelid margin, lower eyelid margin and the face results in hair growth resulting in one selected from the group consisting of longer hair than either latanoprost or latanoprost acid and minoxidil applied alone as monotherapies at the same concentration as they exist in the first composition.

49. The first composition of embodiment 47 comprising latanoprost or latanoprost acid and minoxidil or minoxidil sulphate when applied to the skin results in greater individual hair diameter or circumference than either latanoprost or latanoprost acid and minoxidil applied alone to the skin at the same concentration as monotherapies.

50. The first composition of embodiment 47 comprising latanoprost or latanoprost acid and minoxidil or minoxidil sulphate when applied to the skin results in greater melanin concentration of individual hairs as compared to applying latanoprost or latanoprost acid and minoxidil or minoxidil sulphate applied alone to the skin at the same concentration as monotherapies.

51. A first composition comprising travoprost or travoprost free acid and minoxidil or minoxidil sulphate when applied to the skin results in hair growth resulting in longer hair than either travoprost or travoprost acid and minoxidil or minoxidil sulphate applied alone wherein the concentration of travoprost or travoprost acid and minoxidil or minoxidil sulphate are at the same concentrations as compared to travoprost or travoprost acid and minoxidil or minoxidil sulphate monotherapies.

52. The first composition of embodiment 51 comprising travoprost or travoprost free acid and minoxidil or minoxidil sulphate wherein the application of the first composition to the skin results in greater hair growth as compared to either travoprost or travoprost acid and minoxidil or minoxidil sulphate applied to the skin alone as monotherapies at the same individual concentration as they exist in the first composition.

53. The first composition of embodiment 51 comprising travoprost or travoprost free acid and minoxidil or minoxidil sulphate when applied to the skin results in greater individual hair diameter or circumference as compared to either travoprost or travoprost free acid and minoxidil or minoxidil sulphate applied alone to the skin as monotherapies at the same individual concentration as they exist in the first composition.

54. The first composition of embodiment 47 comprising travoprost or travoprost free acid and minoxidil or minoxidil sulphate when applied to the skin results in greater melanin concentration of individual hairs as compared to applying travoprost or travoprost free acid and minoxidil or minoxidil sulphate applied alone to the skin at the same concentration as monotherapies.

55. A method of stimulating hair growth on the scalp by applying to the scalp a composition selected from the group consisting of one of the embodiments 1-10 or 21-32 or 39-54.

56. A method of stimulating hair growth on the scalp by applying to the scalp a composition selected from the group consisting of one of Formulations I-XXXXX.

57. A method for stimulating hair follicles to increase hair growth and one or more properties selected from the group consisting of individual hair length, individual hair diameter or circumference, individual hair darkness, melanin content of each individual hair, an increase of the ratio of terminal hair to velus hair per square inch of skin, and an increase of dark hair to grey hair in the area of application comprising the application to mammalian skin at the locale of hair follicles of an effective amount of a composition comprising one selected from the group consisting of one of the embodiments 1-10 or 21-32, 39, 41 or 42 or Formulations I-XXXXX.

58. A method for stimulating hair follicles to increase hair growth and one or more properties selected from the group consisting of individual hair length, individual hair diameter or circumference, individual hair darkness, melanin content of each individual hair, increase the ratio of terminal hair to velus hair per square inch of skin, and an increase of dark hair to grey hair in the area of application comprising the application to mammalian skin at the locale of the follicles of an effective amount of a composition comprising one selected from the group consisting of one of the Formulations I-XXXXX.

59. The method of embodiments 57 and 58 wherein the composition is applied to one selected from the group consisting of the scalp, the epidermis layer beneath the eyebrows, lower eyelid margin, upper eyelid margin and the face.

60. A method for increasing the number of terminal hairs on the skin by applying an effective amount on the skin or epidermis of a composition comprising one selected from the group consisting of one of the embodiments 1-10 or 21-32 or 39, 41 or 42 or Formulations I-XXXXX.

61. A method for increasing the number of terminal hairs on the scalp by applying an effective amount to mammalian skin of a composition comprising one selected from the group consisting of one of the of one of the embodiments 1-10 or 21-32 or 39, 41, 42 and 54 or Formulations I-XXXXX.

62. A method of converting gray hair to darker hair by applying an effective amount to mammalian skin of a composition comprising one selected from the group consisting of one of the embodiments 1-10 or 21-32 or 39, 41, 42 and 54 or Formulations I-XXXXX.

63. A method of converting gray hair to darker hair or increasing the melanin content in hair by applying an effective amount to mammalian skin in proximity to the hair follicles of a composition comprising one selected from the group consisting of embodiments 1-10 or 21-32 or 39-54 or one of the of one of the Formulations I-XXXXX.

64. A method of increasing the melanin content of individual hairs by applying an effective amount to mammalian skin in proximity to the hair follicles of a composition comprising one selected from the group consisting of one of the embodiments 1-10 or 21-32 or 39-54 or one of the Formulations I-XXXXX.

65. A method of darkening individual hairs by applying an effective amount to mammalian skin in the area of skin with grey hair of a composition comprising one selected from the group consisting of one of the embodiments 1-10 or 21-32 or 39-54 or one of Formulations I-XXXXX.

66. The method of embodiments 64 and 65 wherein the method increases the melanin content and the keratin content of individual hairs.
67. A method of increasing the diameter or circumference of individual hairs by applying an effective amount to mammalian skin in proximity to the hair follicle of a composition comprising one selected from the group consisting of one of the embodiments 1-10 or 21-32 or 39-54 or one of Formulations I-XXXXX.
68. A method of increasing the diameter, circumference or length of individual hairs by applying an effective amount to hair follicles of a composition comprising one selected from the group consisting of one of the of the embodiments 1-10 or 21-32 or 39-54 or one of Formulations I-XXXXX.
69. The method of embodiments 60-68 wherein the composition is applied to one selected from the group consisting of the scalp, the skin beneath the eyebrows, upper eyelid margin, lower eyelid margin and the face.
70. The method of embodiment 69 wherein the mammal is a human.
71. A method of preventing hair loss in a patient undergoing chemotherapy comprising administering a formulation selected from the group consisting of formulation I-XXXXX or embodiments 1-10 or 21-32 or 39-54 and applying the embodiment or formulation to one selected from the group consisting of the scalp, the epidermis layer beneath the eyebrows, the upper eyelid margin and lower eyelid margin or the face before, during or after chemotherapy.
72. The method of embodiment 71 when the formulation is applied before the patient undergoes chemotherapeutic treatment to reduce the amount of hair loss.
73. The method of embodiment 72 wherein the formulation is applied one selected from the group consisting of 45 days prior to chemotherapeutic treatment, 30 days prior to chemotherapeutic treatment, 25 days prior to chemotherapeutic treatment, 20 days prior to chemotherapeutic treatment, 15 days prior to chemotherapeutic treatment, 10 days prior to chemotherapeutic treatment and either 9, 8, 7, 6, 5, 4, 3, 2 and 1 day prior to chemotherapeutic treatment.
74. The method of embodiments 72 or 73 wherein the formulation is applied from one selected from the group consisting of three times a day, two times a day and once a day.
75. The method of embodiments 71-74 wherein the patient loses less hair from at least one selected from the group consisting of the scalp, eyebrows, eyelashes and face as compared to the patient receiving no formulation for the same period of time.
76. The method of embodiment 75 wherein the hair from the at least one selected from the group consisting of the scalp, eyebrows, eyelashes and face is longer, darker and thicker as compared to the patient receiving no formulation.
77. The method of embodiment 75 wherein the hair from the at least one selected from the group consisting of the scalp, eyebrows, eyelashes and face is more numerous as compared to the patient receiving no formulation.
78. The method of embodiment 71 wherein the formulation is applied while the patient is receiving chemotherapeutic treatment.
79. The method of embodiment 78 wherein the formulation is applied from one selected from the group consisting of three times a day, two times a day and once a day to at least one selected from the group consisting of scalp, eyebrows, eyelashes and face.
80. The method of embodiment 79 wherein the patient loses less hair selected from the group consisting of scalp, eyebrows, eyelashes and face as compared to the patient applying no formulation.
81. The method of embodiments 78 and 79 wherein the hair from the at least one selected from the group consisting of the scalp, eyebrows, eyelashes and face is longer, darker, more numerous and thicker as compared to the patient receiving no treatment.
82. The method of embodiments 78-81 wherein the patient applies the formulation while receiving chemotherapeutic treatment.
83. The method of paragraph 82 wherein the patient applies the formulation after the chemotherapeutic treatment is completed.
84. The method of embodiment 83 wherein the patient applies formulation from one selected from the group consisting of one month, two months, three months, four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months and twenty-four months after completion of chemotherapeutic treatment.
85. The method of embodiment 84 wherein the hair from the at least one selected from the group consisting of the scalp, eyebrows, eyelashes and face is longer, darker, more numerous and thicker as compared to the patient receiving no treatment after chemotherapeutic treatment.
86. The method of embodiment 84 wherein application of the formulations I-XXXXX or embodiments 1-10 or 21-31 or 39-54 to one selected form the group consisting of the scalp, eyebrows, eyelashes and face results in hair entering the anagen phase sooner and/or for a longer duration than if the patient applied no formulation.
87. The method of embodiment 85 wherein application of the formulation to one selected form the group consisting of the scalp, eyebrows, eyelashes and face results in hair entering the anagen phase longer than if the patient applied no formulation.
88. Use of latanoprost or latanoprost acid and minoxidil or minoxidil sulphate in combination for the treatment of hair loss in a patient suffering therefrom.
89. The use of embodiment 88 wherein latanoprost or latanoprost acid is present in a concentration of about 0.08-0.5% w/v, w/w or v/v and minoxidil or minoxidil sulphate is present in a concentration of about 2%-8% w/v, w/w or w/v.
90. The use of embodiment 89 wherein latanoprost or latanoprost acid is present in a concentration of about 0.1-0.3% w/v, w/w or v/v and minoxidil or minoxidil sulphate is present in a concentration of one selected from the group consisting of 1%, 2%, 3%, 4%, 5%, 6%, 7%, 8%, 9% and 10% w/v, w/w or v/v.
91. The use of embodiment 90 wherein latanoprost or latanoprost acid is present in a concentration of about 0.2% w/v, w/w or w/v and minoxidil or minoxidil sulphate is present in a concentration of about 5% w/v, w/w or v/v.
92. The use of embodiment 90 wherein latanoprost or latanoprost is present in a concentration of about 0.3% w/v and minoxidil or minoxidil sulphate is present in a concentration of about 5% w/v, w/w or v/v.

93. The use of embodiment 90 wherein latanoprost is present in a concentration of about 0.8% w/v and minoxidil is present in a concentration of about 4% w/v.

94. The use of embodiments 88-93 wherein the hair loss is at least one selected from the group consisting of scalp hair, eyebrows, eyelashes or facial hair.

95. Use of latanoprost or latanoprost acid and minoxidil or minoxidil sulphate in combination for growing hair in a patient.

96. The use of embodiment 95 wherein the patient is suffering from hair loss.

97. The use of embodiment 95 wherein latanoprost or latanoprost acid is present in a concentration of about 0.08-0.5% w/v, w/w or v/v and minoxidil or minoxidil sulphate is present in a concentration of about 2%-8% w/v, w/w or v/v.

98. The use of embodiment 95 wherein latanoprost or latanoprost acid is present in a concentration of about 0.1-0.3% w/v, w/w or v/v and minoxidil or minoxidil sulphate is present in a concentration of 4%-7% w/v, w/w or v/v.

99. The use of embodiment 95 wherein latanoprost or latanoprost acid is present in a concentration of about 0.2% w/v, w/w or v/v and minoxidil or minoxidil sulphate is present in a concentration of about 4% w/v, w/w or v/v.

100. The use of embodiment 95 wherein latanoprost or latanoprost acid is present in a concentration of about 0.3% w/v, w/w or v/v and minoxidil or minoxidil sulphate is present in a concentration of about 5% w/v, w/w or v/v.

101. The use of embodiment 95 wherein latanoprost or latanoprost acid is present in a concentration of about 0.1% w/v and minoxidil or minoxidil sulphate is present in a concentration of about 5% w/v, w/w or v/v.

102. The use of embodiments 88-93 and 97-100 wherein the hair loss is at least one selected from the group consisting of scalp hair, eyebrows, eyelashes or facial hair.

103. Use of travoprost or travoprost free acid and minoxidil or minoxidil sulphate in combination for the treatment of hair loss in a patient suffering therefrom.

104. The use of embodiment 103 wherein travoprost or travoprost free acid is present in a concentration of about 0.08-0.5% w/v, w/w or v/v and minoxidil or minoxidil sulphate is present in a concentration of about 2%-8% w/v, w/w or v/v.

105. The use of embodiment 103 wherein travoprost or travoprost free acid is present in a concentration of about 0.07%-0.3% w/v, w/w or v/v and minoxidil or minoxidil sulphate is present in a concentration of 4%-7% w/v, w/w or v/v.

106. The use of embodiment 103 wherein travoprost or travoprost free acid is present in a concentration of about 0.2% w/v, w/w or v/v and minoxidil or minoxidil sulphate is present in a concentration of about 5% w/v, w/w or v/v.

107. The use of embodiment 103 wherein travoprost or travoprost free acid is present in a concentration of about 0.3% w/v, w/w or v/v and minoxidil or minoxidil sulphate is present in a concentration of about 5% w/v, w/w or v/v.

108. The use of embodiment 103 wherein travoprost or travoprost free acid is present in a concentration of about 0.1% w/v, w/w or v/v and minoxidil or minoxidil sulphate is present in a concentration of about 5% w/v, w/w or v/v.

109. The use of embodiments 103-108 wherein the hair loss is at least one selected from the group consisting of scalp hair, eyebrows, eyelashes or facial hair.

110. Use of travoprost or travoprost free acid and minoxidil or minoxidil sulphate in combination for growing hair in a patient.

111. The use of embodiment 110 wherein the patient is suffering from hair loss.

112. The use of embodiment 111 wherein travoprost or travoprost free acid is present in a concentration of about 0.08-0.5% w/v, w/w or v/v and minoxidil or minoxidil sulphate is present in a concentration of about 2%-8% w/v, w/w or v/v.

113. The use of embodiment 111 wherein travoprost or travoprost free acid is present in a concentration of about 0.1-0.3% w/v, w/w or v/v and minoxidil or minoxidil sulphate is present in a concentration of 4%-7% w/v, w/w, w/w or v/v.

114. The use of embodiment 95 wherein travoprost or travoprost free acid is present in a concentration of about 0.2% w/v, w/w, or v/v and minoxidil or minoxidil sulphate is present in a concentration of about 5% w/v, w/w or v/v.

115. The use of embodiment 95 wherein travoprost or travoprost is present in a concentration of about 0.3% w/v, w/w, or v/v and minoxidil is present in a concentration of about 5% w/v, w/w, or v/v.

116. The use of embodiment 95 wherein travoprost or travoprost free acid is present in a concentration of about 0.07% or 0.08% w/v, w/w, or v/v and minoxidil or minoxidil sulphate is present in a concentration of about 4%, 5% or 6% w/v, w/w, or v/v.

117. The use of embodiments 103-108 wherein the hair loss is at least one selected from the group consisting of scalp hair, eyebrows, eyelashes or facial hair.

118. Use of bimatoprost and minoxidil or minoxidil sulphate in combination for the treatment of hair loss in a patient suffering therefrom.

119. The use of embodiment 118 wherein bimatoprost is present in a concentration of about 0.08-0.5% w/v, w/w, or v/v and minoxidil or minoxidil sulphate is present in a concentration of about 2%-8% w/v, w/w, or v/v.

120. The use of embodiment 119 wherein bimatoprost is present in a concentration of about 0.1-0.3% w/v, w/w, or v/v and minoxidil or minoxidil sulphate is present in a concentration of 4%-7% w/v, w/w or v/v.

121. The use of embodiment 118 wherein bimatoprost is present in a concentration of about 0.2% w/v, w/v, w/w, or v/v and minoxidil or minoxidil sulphate is present in a concentration of about 5% w/v, w/w or v/v.

122. The use of embodiment 90 wherein bimatoprost is present in a concentration of about 0.3% w/v, w/w or v/v and minoxidil or minoxidil sulphate is present in a concentration of about 5% w/v, w/w or v/v.

123. The use of embodiment 90 wherein bimatoprost is present in a concentration of about 0.1% w/v, w/w or v/v and minoxidil or minoxidil sulphate is present in a concentration of about 5% w/v, w/w or v/v.

124. The use of embodiments 119-123 wherein the hair loss is at least one selected from the group consisting of scalp hair, eyebrows, eyelashes or facial hair.

125. Use of bimatoprost and minoxidil in combination for growing hair in a patient.

126. The use of embodiment 95 wherein the patient is suffering from hair loss.
127. The use of embodiment 119 wherein bimatoprost is present in a concentration of about 0.08-0.5% w/v, w/w or v/v and minoxidil is present in a concentration of about 2%-8% w/v, w/w or v/v.
128. The use of embodiment 127 wherein bimatoprost is present in a concentration of about 0.08% w/v, w/w or v/v and minoxidil or minoxidil sulphate is present in a concentration of 4%-7% w/v, w/w or v/v.
129. The use of embodiment 95 wherein bimatoprost is present in a concentration of about 0.9% w/, w/w or v/v and minoxidil or minoxidil sulphate is present in a concentration of about 4% w/v, w/w or v/v.
130. The use of embodiment 127 wherein bimatoprost is present in a concentration of about 0.3% w/v, w/w or v/v and minoxidil or minoxidil sulphate is present in a concentration of about 5% w/v, w/w or v/v.
131. The use of embodiment 127 wherein bimatoprost is present in a concentration of about 0.1% w/v and minoxidil or minoxidil sulphate is present in a concentration of about 4% w/v, w/w or v/v.
132. The use of embodiments 126-131 wherein the hair loss is at least one selected from the group consisting of scalp hair, eyebrows, eyelashes or facial hair.
133. A composition for use in the treatment of hair loss comprising about 0.05%-0.5% w/v, w/w or v/v of one selected from the group consisting of latanoprost and latanoprost acid and 1%-8% w/v, w/w or v/v minoxidil.
134. The composition of embodiment 133 wherein the composition has about 0.3% w/v, w/w or v/v latanoprost or latanoprost acid and about 5% w/v, w/w or v/v minoxidil or minoxidil sulphate.
135. The composition of embodiment 133 wherein the composition has about 0.07% w/v, w/w or v/v latanoprost or latanoprost acid and about 4-6% w/v, w/w or v/v minoxidil or minoxidil sulphate.
136. The composition of embodiment 133 further comprising oleyl alcohol or ethanol.
137. The composition of embodiment 136 further comprising propylene glycol.
138. The composition of embodiment 133 wherein the hair loss is due to androgenetic alopecia.
139. The composition of embodiment 137 wherein the hair loss is due to alopecia areata.
140. The composition of embodiment 137 further comprising acetic acid one selected from the group consisting of polysorbate 60 and polyoxyethylene lauryl alcohol.
141. The composition of embodiment 134 further comprising acetic acid one selected from the group consisting of polysorbate 60 and polyoxyethylene lauryl alcohol.
142. The composition of embodiment 137 further comprising ethanol and at least one selected form the group consisting of propylene glycol and polysorbate 80.
143. The composition of embodiment 142 wherein ethanol is present in a concentration of about 25%-50% w/v.
144. The composition of embodiment 143 wherein the composition further comprises oleyl alcohol.
145. The composition of embodiment 144 further comprising diethylene glycol monoethyl ether.
146. The composition of embodiment 134 further comprising ethanol, propylene glycol, water and at least one selected from the group consisting of benzyl alcohol, oleic acid, oleyl alcohol and polyoxyethylene lauryl alcohol.
147. The composition of embodiment 135 wherein the composition comprises ethanol, propylene glycol, polysorbate, water and at least one selected from the group consisting of acetic acid, oleic acid and oleyl alcohol.
148. The composition of embodiment 147 wherein the composition comprises acetic acid from about 0.1-0.5% w/v, w/w or v/v.
149. The composition of embodiment 147 wherein the composition comprises propylene glycol from about 5%-60% w/v, w/w or v/v.
150. The composition of embodiment 133 wherein the composition comprises ethanol, propylene glycol, polysorbate, water and at least one selected from the group consisting of acetic acid, oleic acid and oleyl alcohol.
151. A method of growing hair on the scalp by applying the formulation of embodiment 134 to the scalp at least once a day wherein the area of the scalp where the formulation is applied will grow hair to a greater extent than an area of the scalp receiving no formulation.
152. A method of growing hair comprising administering the formulation of embodiment 135 to the skin wherein the formulation causes hair in the telogen phase area of application to the scalp to enter the anagen phase sooner than areas of the scalp not receiving formulation.
153. A method of enhancing nail growth or treating brittle nail syndrome in a patient suffering therefrom comprising administering to the patient a formulation selected from embodiments 1-10 or 21-31 or 35-54 and Formulations I-XXXXX topically applied to the fingernails or cuticles of a patient at least once a day.
154. The method of embodiment 153 wherein the method is useful for treating a disorder of the toenail or fingernail selected from the group consisting of nail psoriasis, psoriatic nail dystrophy, brittle nail syndrome, increasing nail length and thickness, onychia, onychiagryposis, onychia trophia, onychocryptosis, onychodystrophy, onychogryposis, onycholysis, onychomadesis, onychauxis, onychomycosis, onychorrhexis, tinea unguium, onychophosis, onychoptosis, paronychia, pseudomonas, pterygium and pterygium inversum unguis, koilonychia, subungual hematoma or other trauma to the nail, folic acid deficiency, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, bleeding associated with rheumatoid arthritis, beau's lines, and Mee's lines associated with certain kinds of poisoning.
155. A method of stimulating melanogenesis in melanocytes in cells in and around or in close proximity to the hair follicle while simultaneously causing hair growth by administering one of embodiments 1-10 or 21-31 or 35-54 or one of Formulations I-XXXXX to hair follicles wherein the melancytes will enter into melanogenesis at a faster onset as compared to none of the embodiments or Formulations being applied to the hair follicle.
156. The method embodiment 155 wherein the melanosomes in the melanocytes produce more melanin as compared to none of the embodiments or Formulations being topically applied to the hair follicles.
157. The method of embodiment 155 wherein the melanosomes in the melanocytes produce more of one selected from the group consisting of black eumelanin, brown eumelanin, yellow pheomelanin and red-brown pheomelanin as compared to none of the embodiments or Formulations being applied to the hair follicles.
158. A method of hair growth wherein applying one selected from the group of embodiments 5, 6, 7, 18, 19, 20, 23, 24-26, 44, 45, 47, 48, 49, 50, 88-93, 95, 97-101 results in new hair growth which is darker as compared to no formulation being applied.
159. The method of embodiment 158 wherein applying one selected from the group of embodiments 5, 6, 7, 18, 19, 20, 23, 24-26, 44, 45, 47, 48, 49, 50, 88-93, 95, 97-101 results in new hair growth which is darker as compared to the same compositions in embodiments 5, 6, 7, 18, 19, 20, 23, 24-26, 44, 45, 47, 48, 49, 50, 88-93, 95, 97-101 but wherein bimatoprost is exchanged for latanoprost in the individual embodiments and at the same concentration.
160. The method of embodiment 158 wherein applying one selected from the group of embodiments 5, 6, 7, 18, 19, 20, 23, 24-26, 44, 45, 47, 48, 49, 50, 88-93, 95, 97-101 results in new hair growth which is darker as compared to the same compositions in embodiments 5, 6, 7, 18, 19, 20, 23, 24-26, 44, 45, 47, 48, 49, 50, 88-93, 95, 97-101 but wherein travoprost is exchanged for latanoprost in the individual embodiments and at the same concentration to the hair follicle.
161. A method of stimulating keratogenesis in keratinocytes in cells in and around or in close proximity to the hair follicle while simultaneously causing hair growth by administering one of embodiments 1-10 or 21-31 or 35-54 or one of Formulations I-XXXXX to hair follicles wherein the keratinocytes will enter into keratogenesis at a faster onset and/or a longer duration as compared to none of the embodiments or Formulations being applied.
162. The method embodiment 161 wherein the keratinocytes produce hair which is thicker or larger in diameter and/or circumference as compared to none of the embodiments or Formulations being topically applied to the hair follicles.
163. A method of hair growth wherein applying one selected from the group of embodiments 5, 6, 7, 18, 19, 20, 23, 24-26, 44, 45, 47, 48, 49, 50, 88-93, 95, 97-101 results in new hair growth which is one selected from the group consisting of thicker, longer, greater in diameter and greater in circumference as compared to no formulation being applied.
164. The method of embodiment 163 wherein applying one selected from the group of embodiments 5, 6, 7, 18, 19, 20, 23, 24-26, 44, 45, 47, 48, 49, 50, 88-93, 95, 97-101 results in new hair growth which is one selected from the group consisting of thicker, longer, greater in diameter and greater in circumference as compared to the same compositions in embodiments 5, 6, 7, 18, 19, 20, 23, 24-26, 44, 45, 47, 48, 49, 50, 88-93, 95, 97-101 but wherein bimatoprost is exchanged for latanoprost in the individual embodiments and at the same concentration.
165. The method of embodiment 163 wherein applying one selected from the group of embodiments 5, 6, 7, 18, 19, 20, 23, 24-26, 44, 45, 47, 48, 49, 50, 88-93, 95, 97-101 results in new hair growth which is one selected from the group consisting of thicker, longer, greater in diameter and greater in circumference as compared to the same compositions in embodiments 5, 6, 7, 18, 19, 20, 23, 24-26, 44, 45, 47, 48, 49, 50, 88-93, 95, 97-101 but wherein travoprost is exchanged for latanoprost in the individual embodiments and at the same concentration.
166. A method of increasing hair growth by applying one of embodiments 1-10 or 21-31 or 35-54 or one of Formulations I-XXXXX to hair follicles and applying infrared radiation to the hair follicles.
167. The method of embodiment 166 wherein the infrared radiation is applied after embodiments 1-10 or 21-31 or 35-54 or one of Formulations I-XXXXX is applied to the hair follicles.
168. The method of embodiment 167 wherein the infrared radiation is applied from above the hair follicle by a device for a period of one selected from the group consisting of 1, 2, 3, 4, 5, 6, 7, 8, 9, 10, 11, 12, 13, 14, 15, 16, 17, 18, 19, 20, 21, 22, 23 and 24 hours.
169. A composition comprising tafluprost and minoxidil.
170. A composition for use in the treatment of hair loss comprising about 0.05%-0.3% w/w, w/v, or v/v tafluprost and 1%-5% w/w, w/v, or v/v minoxidil.
171. The composition of embodiments 169 and 170, the composition further comprising polyethylene glycol or propylene glycol and ethanol.
172. The composition of embodiments 169, 170 and 171 further comprising 0.1% w/v tafluprost and 5% w/v minoxidil.
173. A composition for use in treating hair loss comprising tafluprost and finasteride.
174. The composition of embodiment 173 comprising 0.05% w/v-0.3% w/v tafluprost and 0.05% w/v-0.3% w/v finasteride.
175. A composition for use in treating hair loss comprising tafluprost and cyclosporine.
176. The composition of embodiment of claim 175 comprising 0.05%-0.1% w/w, w/v, or v/v tafluprost and 0.05%-0.1% w/w, w/v, or v/v cyclosporine.
177. The composition of embodiment 176 wherein the cyclosporine is cyclosporine A.

4. BRIEF DESCRIPTION OF THE DRAWINGS

5. DETAILED DESCRIPTION OF THE INVENTION

A. Prostaglandin Analog

Figure 1:
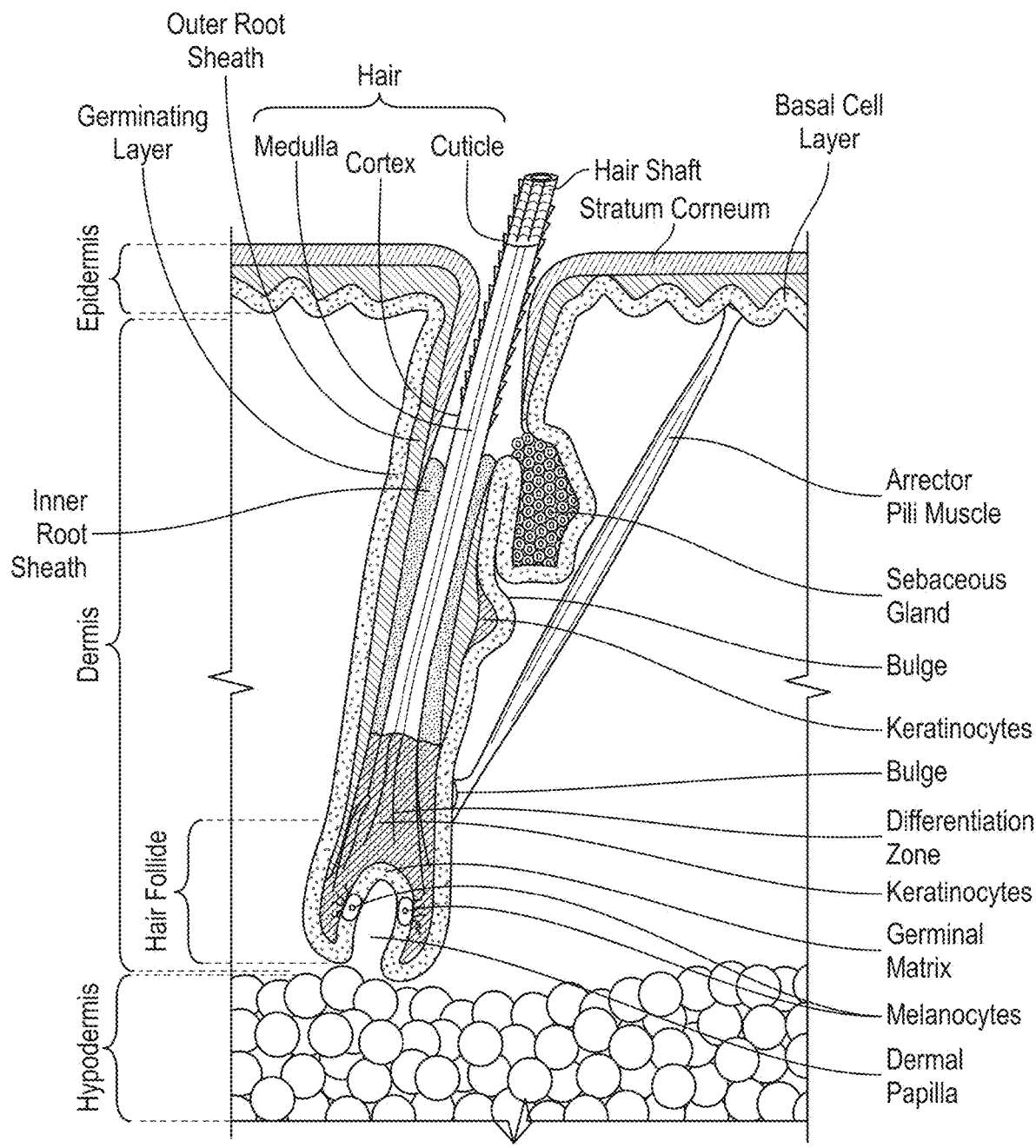
FIG. 1 is a description of the anatomy of a hair follicle including the surrounding tissue.
Figure 2:
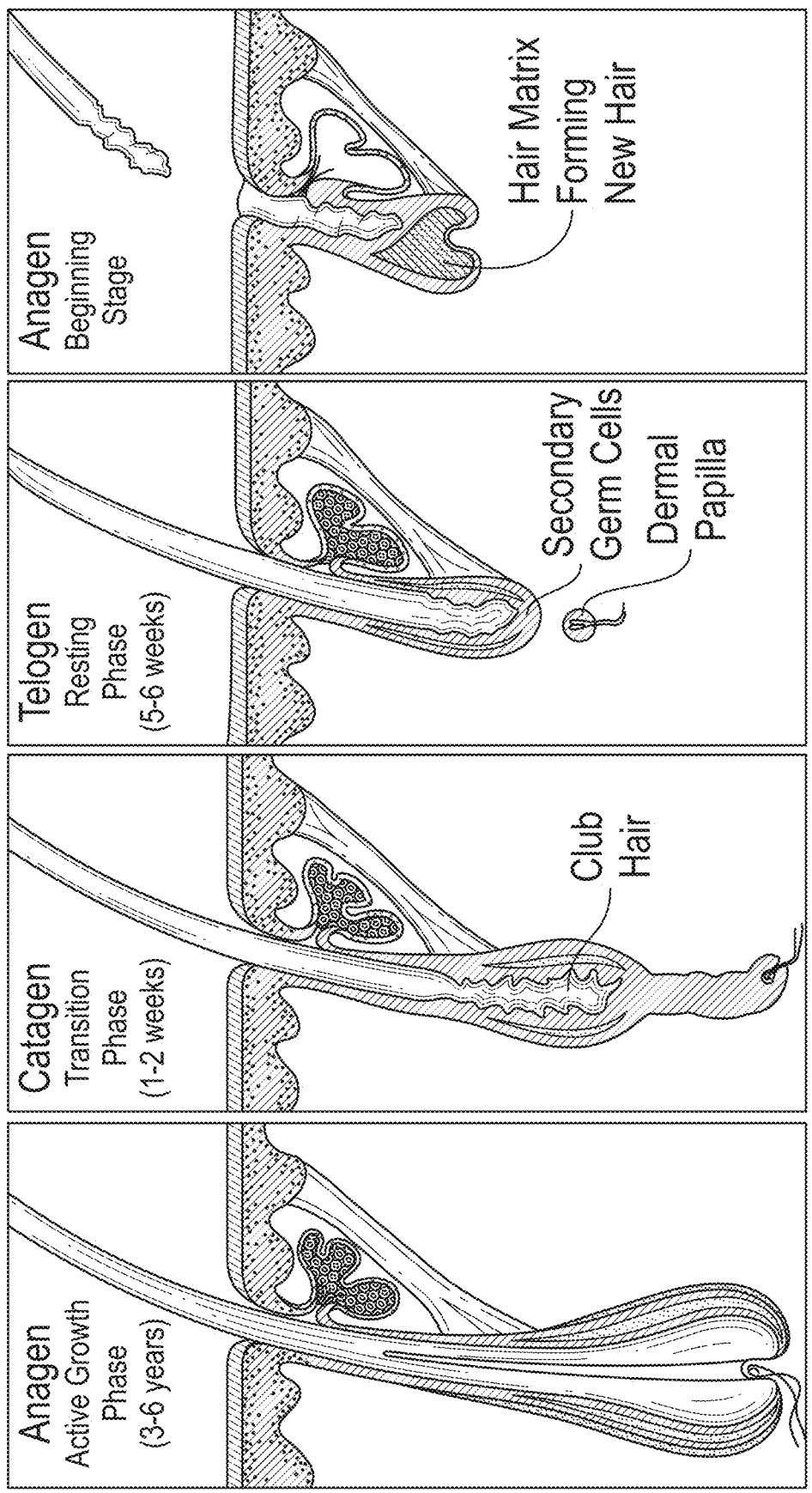
FIG. 2 is a description of the various phases of hair growth.
Figure 3:
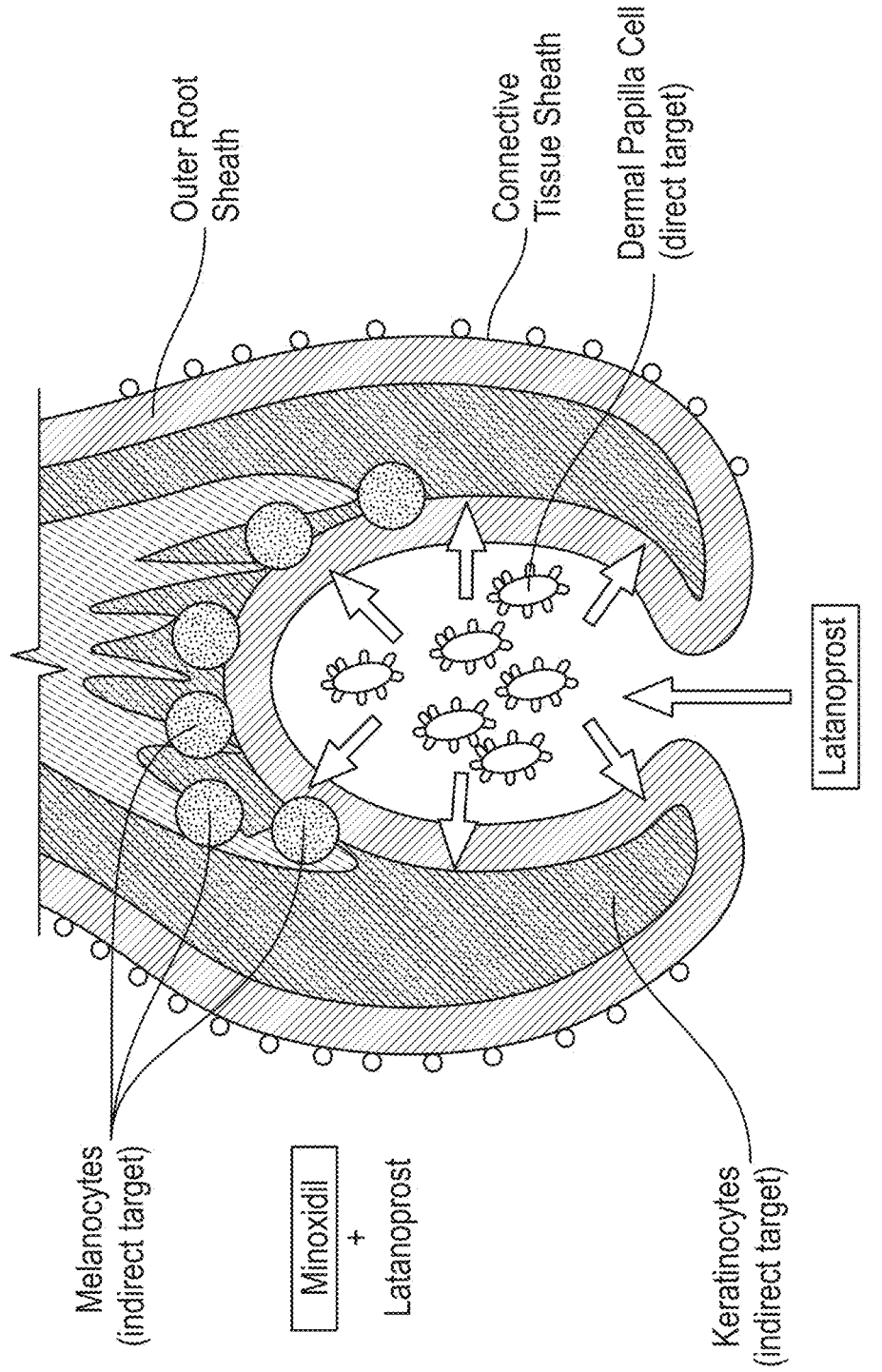
FIG. 3 is the proposed mechanism of action of one of the formulations of the invention.

Prostaglandin analogs of the present invention include latanoprost, travoprost, uenoprost isopropyl ester, the free acids of those compounds and other prostaglandin analogues known in the literature. Bimatoprost is actually a prostamide and is not a prostaglandin analog.

Compounds of the present invention may be represented generally by the formula I:

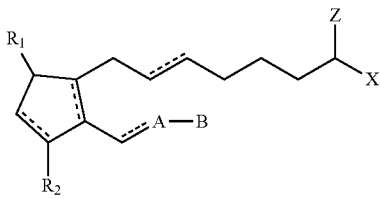

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or akylcarboxy groups wherein said alkyl radical comprises from one to six carbon atoms;

B is a cycloalkyl radical having from three to seven carbon atoms, which may be unsubstituted or substituted with one selected from the group consisting of H, methyl, or perfluoromethyl, or an aryl radical, selected from the group consisting of hydrocarbyl aryl and heteroaryl radicals having from four to ten carbon atoms wherein a heteroatom may be selected from the group consisting of nitrogen, oxygen, halogen atoms, e.g. fluorine, lower alkyl radical having from one to six carbon atoms and optionally substituted with a halogen, and sulfur atoms;

X is a radical selected from the group consisting of —O($R^4$) and —N($R^4$)$_2$ wherein $R^4$ may be the same or different and is independently selected from the group consisting of hydrogen, —$CH_3$, a lower alkyl radical having from one to six carbon atoms optionally substituted with H or —$CH_3$, $R^5$—C— or $R^5$—O—C— wherein $R^5$ is a lower alkyl radical having from one to six carbon atoms;

Z is =O or represents 2 hydrogen radicals; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)m$R_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —O$R^4$. That is, the cycloalkyl or hydrocarbyl aryl or heteroaryl radical is not substituted with a pendant radical having an atom other than carbon or hydrogen.

Compounds of the present invention may also be represented by the following general formula II:

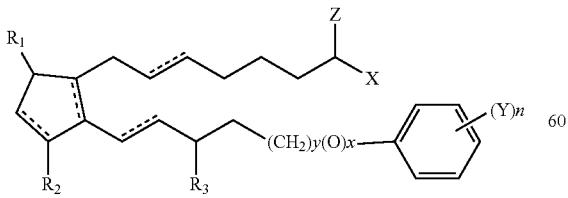

wherein the dashed bonds represent a single or double bond which can be in the cis or trans configuration, wherein y is 0 or 1, x is 0 or 1 and x and y are not both 1, Y is a radical selected from the group consisting of alkyl, halogen, e.g. fluoro, chloro, etc., nitro, amino, thiol, hydroxy, alkyloxy, alkylcarboxy, halogen substituted alkyl such as perfluoromethyl, perfluoroethyl and perfluoropropyl wherein said alkyl radical comprises from one to six carbon atoms, and n is 0 or an integer of from 1 to about 3 and $R_3$ is =O, —OH or —O(CO)$R_6$ wherein $R_6$ is as defined above. Preferably, n is 1 or 2.

X is a radical selected from the group consisting of —O($R^4$) and —N($R^4$)$_2$ wherein $R^4$ may be the same or different and is independently selected from the group consisting of hydrogen, —$CH_3$, a lower alkyl radical having from one to six carbon atoms optionally substituted with H or —$CH_3$, $R^5$—C— or $R^5$—O—C— wherein $R^5$ is a lower alkyl radical having from one to six carbon atoms;

Z is =O or represents 2 hydrogen radicals; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)m$R_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —O$R^4$. That is, the cycloalkyl or hydrocarbyl aryl or heteroaryl radical is not substituted with a pendant radical having an atom other than carbon or hydrogen.

Compounds may also be represented by the general formula (III).

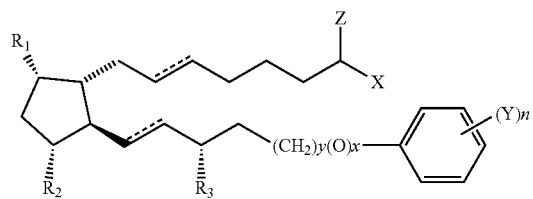

Compounds of the present invention may also be represented by the general Formula (IV):

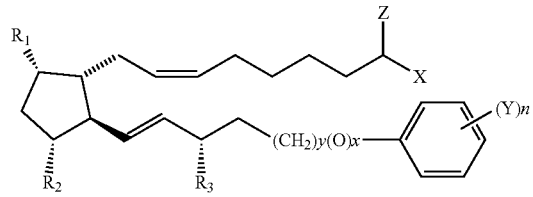

Or represented by the general Formula V:

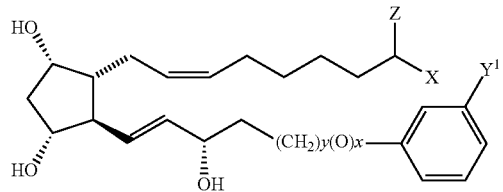

In all of the above formulae, the dotted lines on bonds between carbons 5 and 6 (C-5), between carbons 13 and 14 (C-13), between carbons 8 and 12 (C-8), and between carbons 10 and 11 (C-10), indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

y is 0 or 1, x is 0 or 1 and x and y are not both 1, Y is a radical selected from the group consisting of alkyl, halogen, e.g. fluoro, chloro, etc., nitro, amino, thiol, hydroxy, alkyloxy, alkylcarboxy, halogen substituted alkyl such as perfluoromethyl, perfluoroethyl and perfluoropropyl wherein said alkyl radical comprises from one to six carbon atoms, etc. and n is 0 or an integer of from 1 to about 3 and $R_3$ is =O, —OH or —O(CO)$R_6$ wherein $R_6$ is as defined above. Preferably, n is 1 or 2.

X is a radical selected from the group consisting of —O($R^4$) and —N($R^4$)$_2$ wherein $R^4$ may be the same or different and is independently selected from the group consisting of hydrogen, —CH$_3$, a lower alkyl radical having from one to six carbon atoms optionally substituted with H or —CH$_3$, $R^5$—C— or $R^5$—O—C— wherein $R^5$ is a lower alkyl radical having from one to six carbon atoms;

Z is =O or represents 2 hydrogen radicals; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)$_m$R$_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —OR$^4$. That is, the cycloalkyl or hydrocarbyl aryl or heteroaryl radical is not substituted with a pendant radical having an atom other than carbon or hydrogen.

In the compounds used in accordance with the present invention, compounds having the C-9 or C-11 or C-15 substituents in the α or β configuration are contemplated. As hereinabove mentioned, in all formulas provided herein broken line attachments to the cyclopentane ring indicate substituents in the α-configuration. Thickened solid line attachments to the cyclopentane ring indicate substituents in the α-configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —(CH$_2$)$_m$R$_7$, wherein n is 0 or an integer of from 1 to 10, $R_7$ is an aliphatic ring from about 3 to about 7 carbon atoms, or an aromatic or heteroaromatic ring. The "aliphatic ring" may be saturated or unsaturated, and preferably is a saturated ring having 3-7 carbon atoms, inclusive. As an aromatic ring, $R_7$ preferably is phenyl, and the heteroaromatic rings have oxygen, nitrogen or sulfur as a heteroatom, i.e. $R_7$ may be thienyl, furanyl, pyridyl, etc. Preferably m is 0 or an integer of from 1 to 4.

Z is =O or represents two hydrogen atoms.

X may be selected from the group consisting of —O($R^4$) and —N($R^4$)$_2$ wherein $R^4$ may be the same or different and is independently selected from the group consisting of hydrogen, —CH$_3$, a lower alkyl radical having from one to six carbon atoms optionally substituted with H or —CH$_3$,

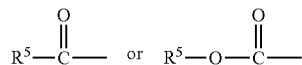

wherein $R^5$ is a lower alkyl radical having from one to six carbon atoms.

1) Latanoprost

Latanoprost has the following structure:

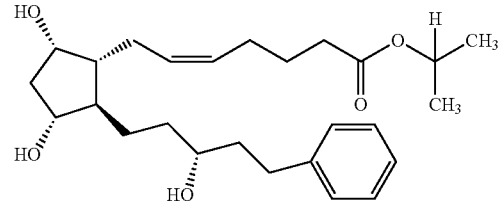 [SMILES: CC(C)OC(=O)CCC/C=C\C[C@@H]1[C@@H](CC[C@@H](O)CCc2ccccc2)[C@H](O)C[C@@H]1O]

Latanoprost is a prostaglandin analogue and is in fact a prodrug with its acid form (Latanoprost acid) being biologically active:

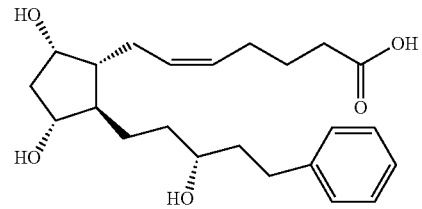 [SMILES: O=C(O)CCC/C=C\C[C@@H]1[C@@H](CC[C@@H](O)CCc2ccccc2)[C@H](O)C[C@@H]1O]

Latanoprost is an isopropyl ester, and is a prodrug which converts to latanoprost free acid by r[(3R)-3-hydroxy-5-phenylpentyl]cyclopentyl]hept-5-enoic acid. The free acid form of latanoprost is two-hundred times more potent than latanoprost as an FP receptor ligand for the human recombinant FP receptor. Latanoprost free acid is a potent FP receptor agonist with an EC$_{50}$ of 3.6 nM for human FP receptors, which is twice the potency of PGF$_{2\alpha}$. The efficacy of PG analog esters for the treatment of glaucoma or elevated IOP correlates closely with the FP receptor binding affinity of the free acid. Other forms of latanoprost which may be used in the present invention include 15-keto latanoprost, 15(S)-latanoprost, 5-trans latanoprost, latanoprost-d4, latanoprost lactol and latanoprost ethyl amide-d4.

Latanoprost is a molecule that is poorly dissolved in water but is generally fat soluble. Latanoprost is more fat soluble than bimatoprost. If an organic solvent-free solution of latanoprost is needed, it can be prepared by evaporating the methyl acetate and directly dissolving the neat oil in aqueous buffers. The solubility of latanoprost in PBS (pH 7.2) is approximately 50 μg/mL. For maximum solubility in aqueous buffers, latanoprost should first be dissolved in ethanol or propylene glycol and then diluted with the aqueous buffer of choice. Latanoprost has a solubility of 400 μg/mL in a 1:4 solution of ethanol:PBS (pH 7.2) using this method. In acidic or basic aqueous solutions, latanoprost is stable for no more than 48 hours and in neutral aqueous solutions it has shown to be stable for up to one month at room temperature. Latanoprost is the isopropyl ester of 17-phenyl-13,14-dihydro prostaglandin F2a (17-phenyl-13,14-dihydro PGF2a).

Sufficient amount of solubility can be obtained even at the highest concentration (5%) that can be used in propylene glycol, methanol, ethanol and 2-propanol. Moreover it has been noted that latanoprost can be dissolved in a suitable dissolving agent such as alcohol (propylene glycol, methanol, ethanol, 2-propanol) and other co-solvent such as some aromatic and polyhydric alcohols (cetyl alcohol, stearyl alcohol, benzyl alcohol, glyceryl mono-oleate, POE stearate, polyoxyethylene lauryl alcohol, 1-3butylene glycol, glycerol).

Latanoprost including 15-keto latanoprost, 15(S)-latanoprost, 5-trans latanoprost, latanoprost-d4, latanoprost lactol, latanoprost ethyl amide-d4 and latanoprost acid may be present in the formulations of the present invention in the following concentrations: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, %, 0.11%, 0.12%, 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75/o, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9, 4.0%, 4.1%, 4.2%, 4.3%, 4.4%, 4.5%, 4.6%, 4.7%, 4.8%, 4.9%, 5.0%, 6.0%, 7.0%, 8.0%, 9.0%, 10%, 11%, 12%, 13%, 14%, 15%, 16%, 17%, 18%, 19%, 20%, 21%, 22%, 23%, 24% and 25% w/w, w/v or v/v.

Latanoprost, including 15-keto latanoprost, 15(S)-latanoprost, 5-trans latanoprost, latanoprost-d4, latanoprost lactol, latanoprost ethyl amide-d4 and latanoprost acid may be present in the formulations of the present invention alone or in combination with other prostaglandin analogs. Latanoprost including 15-keto latanoprost, 15(S)-latanoprost, 5-trans latanoprost, latanoprost-d4, latanoprost lactol, latanoprost ethyl amide-d4 and latanoprost acid may be present in the formulations of the present invention alone or in combination with topical minoxidil or minoxidil sulphate or topical or oral finasteride. Latanoprost, including 15-keto latanoprost, 15(S)-latanoprost, 5-trans latanoprost, latanoprost-d4, latanoprost lactol, latanoprost ethyl amide-d4 and latanoprost acid may be present in the formulations of the present invention alone or in combination with cyclosporine formulas I, II and III.

2) Travoprost

Travoprost is a synthetic prostaglandin F analogue and isopropyl ester of the biologically active free acid. Its chemical name is [1R [1α(Z),2β(1E,3R*),3α,5α]]-7-[3,5-Dihydroxy-2-[3-hydroxy-4-[3 (trifluoromethyl)phenoxy]-1-butenyl]cyclopentyl]-5-heptenoic acid, 1-methylethylester. It has a molecular formula of $C_{26}H_{35}F_3O_6$ and a molecular weight of 500.55:

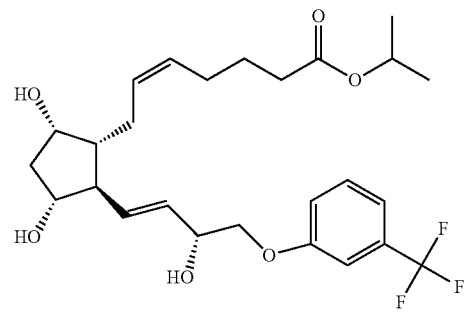 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

Travoprost free acid has the following structure:

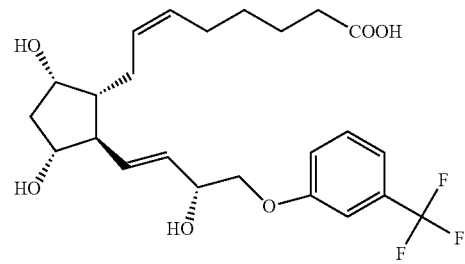 [SMILES: O=C(O)CCCC/C=C\C[C@@H]1[C@@H](/C=C/[C@@H](O)COc2cccc(C(F)(F)F)c2)[C@H](O)C[C@@H]1O]

Travoprost and travoprost free acid may be present in the formulations of the present invention in the following concentrations: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%,%, 0.11%. 0.12%. 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0%, 10%, 11%, 12%, 13%, 14%, 15%, 16%, 17%, 18%, 19%, 20%, 21%, 22%, 23%, 24% and 25% w/w, w/v or v/v.

Travoprost and travoprost free acid may be present in the formulations of the present invention alone or in combination with other prostaglandin analogs or other hair growth compounds. Travoprost and travoprost free acid may be present in the formulations of the present invention alone or in combination with topical minoxidil or minoxidil sulphate or topical or oral finasteride. Travoprost and travoprost free acid may be combined with cyclosporine formulas I, II or II.

3) Uenoprostone Isopropyl Ester

Unoprostone isopropyl ester has the following structure:

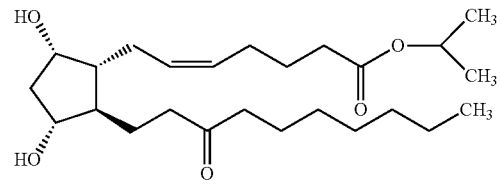 [SMILES: CCCCCCCC(=O)CC[C@@H]1[C@@H](C/C=C\CCCC(=O)OC(C)C)[C@@H](O)C[C@H]1O]

Uenoprostone isopropyl ester is a prodrug which converts to uenoprostone free acid which has the following structure:

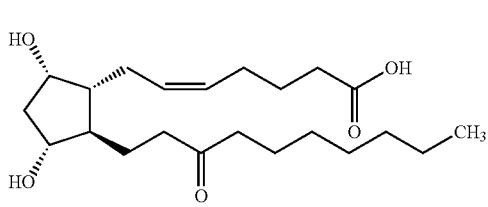 [SMILES: CCCCCCCC(=O)CC[C@@H]1[C@@H](C/C=C\CCCC(=O)O)[C@@H](O)C[C@H]1O]

Uenoprostone isopropyl ester and uenoprostone free acid while efficacious at lowering intraocular pressure, have been shown to cause no hair growth and in fact may inhibit hair growth (McCarey B. E., Kapik B. M., Kane F. E. [2004]). Low incidence of iris pigmentation and eyelash changes in two randomized clinical trials was reported with uenoprostone isopropyl 0.15%. (Ophthalmology 111, 1480-1488). This demonstrates that unpredictability of prostaglandin anologs for use in growing hair and that many prostaglandin analogs do not grow hair and may inhibit hair growth.

4) Bimatoprost

Bimatoprost is a prostamide from a group of biological lipids, which are related to prostaglandins, but contain a terminal ethanolamide group and which target different receptors than prostaglandin analogues such as latanoprost or travoprost. Technically, bimatoprost is not considered to be a prostaglandin analog but is a prostamide. Bimatoprost may be represented by the following formula:

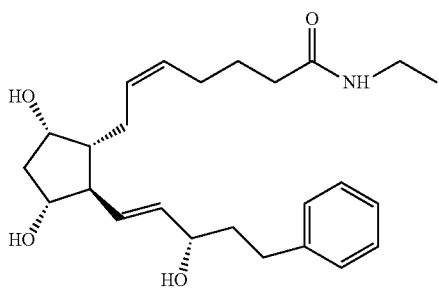 [SMILES: CCNC(=O)CCC/C=C\C[C@@H]1[C@@H](/C=C/[C@@H](O)CCc2ccccc2)[C@H](O)C[C@@H]1O]

Bimatoprost is not a prodrug and is not converted into another compound or in only small amounts (under 5%) are believed converted into bimatoprost free acid. Bimatoprost differs from the other compounds in that it is an amide:

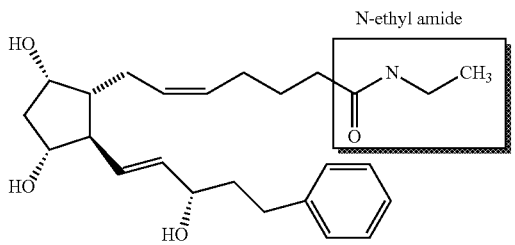

While there is a bimatoprost free acid:

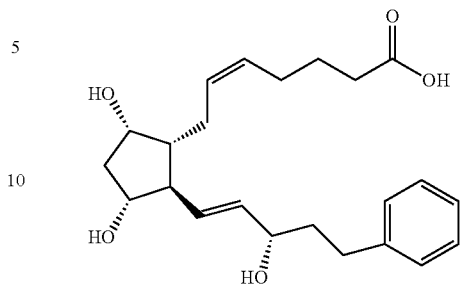

bimatoprost is believed to exert its biological activity as a hair growth agent as an ethyl amide and not as a free acid. This is in contrast to latanoprost and travoprost which are prodrugs and exert their physiological effects on different receptors than bimatoprost which illustrates the lack of predictability of bimatoprost, latanoprost, travoprost and uenoprostone isopropyl ester in their use in stimulating hair growth. Bimatoprost and latanoprost have significantly differing solubilities and pharmacological properties. Bimatoprost salt forms include a tromethamine salt form. For example, LUMIGAN® 0.03% w/v, a topical solution for lowering elevated intraocular pressure and treating glaucoma, the first approved use of bimatoprost, has a clinical concentration of bimatoprost of 0.03% w/v. XALATAN®, a topical solution for lowering elevated intraocular pressure and treating glaucoma, the first approved use of latanoprost, has a clinical concentration of 0.005% w/v.

The action of prostamides such as bimatoprost involve mechanisms different from prostanoid FP receptor-mediated responses with ligands such as latanoprost and travoprost. The effect of bimatoprost in monkeys with elevated intraocular pressure model of glaucoma has been shown to be additive to that of latanoprost ("Additivity of Bimatoprost or Travoprost to Latanoprost in Glaucomatous Monkey Eyes", Gagliuso et al., 2004). Pharmacological distinctions between latanoprost and bimatoprost have been demonstrated. Some human patients suffering from glaucoma who were non-responsive to latanoprost were found responsive to bimatoprost in reducing elevated intraocular pressure ("Effect of bimatoprost on patients with primary open-angle glaucoma or ocular hypertension who are nonresponders to latanoprost" Gandolfi 2003). It appears highly likely that latanoprost and bimatoprost interact with different receptors in the eye and in hair follicles.

Bimatoprost and bimatoprost free acid may be present in the following concentrations: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, %, 0.11%, 0.12%, 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0%, 10%, 11%, 12%, 13%, 14%, 15%, 16%, 17%, 18%, 19%, 20%, 21%, 22%, 23%, 24% and 25% w/w, w/v or v/v.

Bimatoprost and bimatoprost free acid may be present in the formulations of the present invention alone or in combination with other prostaglandin analogs. Bimatoprost may be combined with topical minoxidil or minoxidil sulphate or with topical or oral finasteride and may be combined with cyclosporine I, II or III.

The following U.S. patents and patent publications are herein incorporated by reference in their entireties: U.S. Pat. Nos. 8,038,988; 6,262,105; 7,388,029; 6,403,649; 9,750,750; 9,149,484; 9,101,550; 9,700,503; 6,946,120; 5,030,442; 5,030,442; 4,828,837; 7,803,357; 7,749,489; 6,465,514; 4,596,812; 7,442,369; 5,620,980; 5,225,189; 4,820,512; 6,596,266; and, 5,834,014.

U.S. Patent Publications 20160136071; 20160228345; 20050079139; 20100210720; 20050079139; 20080206156; 20080206156; and, 20040082660.

B. Cyclosporines

Cyclosporine occurs naturally and was isolated from the fungus *Tolypocladin inflatum* in 1971. Cyclosporine is an immunosuppressant and is used in Crohn's disease, nephrotic syndrome, rheumatoid arthritis, in organ transplants to prevent rejection and treatment of dry eye disease. 6,254,860; 6,350,442; and 7,368,436, the disclosure of each of which are incorporated by reference in their entireties.

In general, commercially available cyclosporines may contain a mixture of several individual cyclosporines which all share a cyclic peptide structure consisting of eleven amino acid residues with a total molecular weight of about 1,200 Daltons, but with different substituents or configurations of some of the amino acids. Thus the present invention also contemplates mixtures of different types of cyclosporine or cyclosporine components. The term "cyclosporine component" as used herein is intended to include any individual member of the cyclosporine group, salts thereof, derivatives thereof, analogs thereof and mixtures thereof, as well as mixtures of two or more individual cyclosporines salts thereof, derivatives thereof analogs thereof and mixtures thereof.

Particularly preferred cyclosporine components include, without limitation, cyclosporine A, derivatives of cyclosporine A, salts of cyclosporine A and the like and mixtures thereof. Cyclosporine A is an especially useful cyclosporine component.

The chemical structure for cyclosporine A is represented by Formula 1:

Formula I

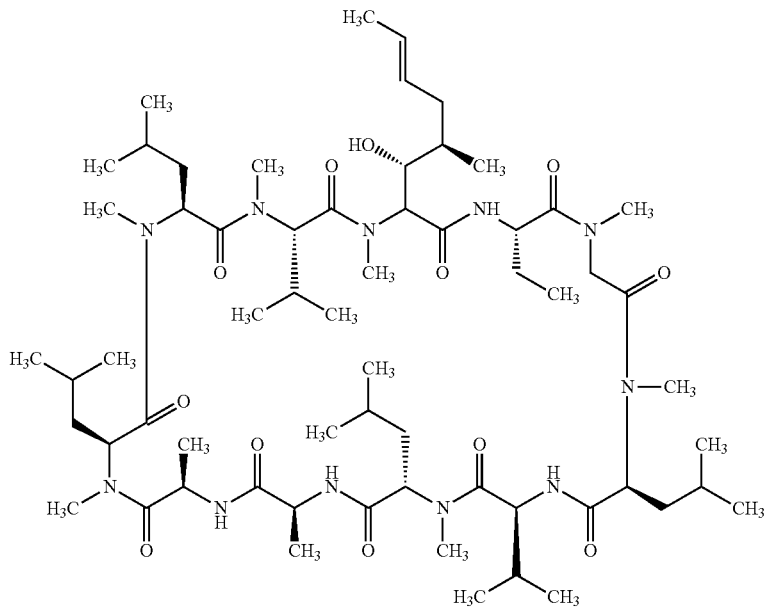

Cyclospormes are a group of nonpolar cyclic oligopeptides with known immunosuppressant activity. Cyclosporine A, along with several other minor metabolites, as well as cyclosporine B, C, D, E, F, G, H, I, J, K, L, M, N, O, P, Q, R, S, T, U, V, W, X, Y and Z, have been identified. In addition, derivatives, salts and the like of such cyclosporines and a number of synthetic analogs have been prepared and may be useful in the present invention. The use of cyclosporine A and cyclosporine A derivatives to treat various ophthalmic conditions, has been the subject of various patents, for example U.S. Pat. Nos. 5,474,979;

As used herein, the term "derivatives" of a cyclosporine refer to compounds having structures sufficiently similar to the cyclosporine so as to function in a manner substantially similar to or substantially identical to the cyclosporine, for example, cyclosporine A, in the present compositions and methods. Included, without limitation, within the useful cyclosporine A derivatives are those selected from ((R)-methylthio-Sar)$^3$-(4'-hydroxy-MeLeu) cyclosporine A, ((R)-(Cyclo)alkylthio-Sar)$^3$-(4'-hydroxy-MeLeu)$^4$-cyclosporine A, and ((R)-(Cyclo)alkylthio-Sar)$^3$-cyclosporine A derivatives described below.

These cyclosporine derivatives are represented by the following generalformulas (II) and (III), respectively:

Formula II

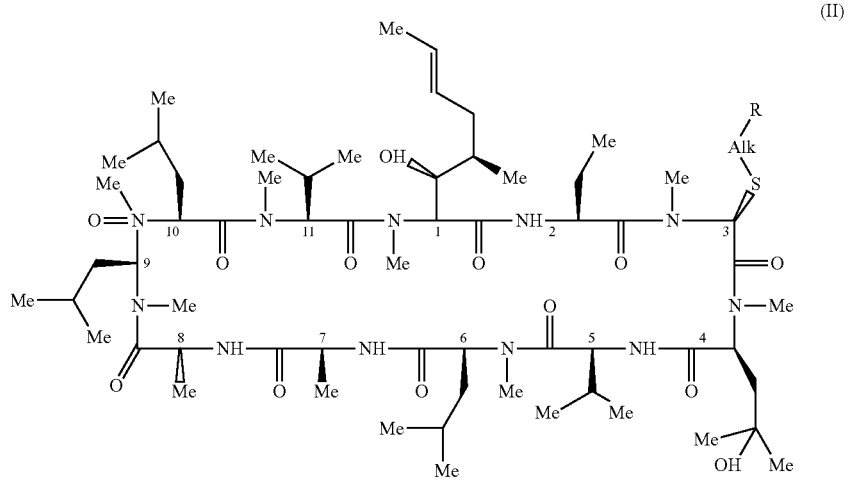

Formula III

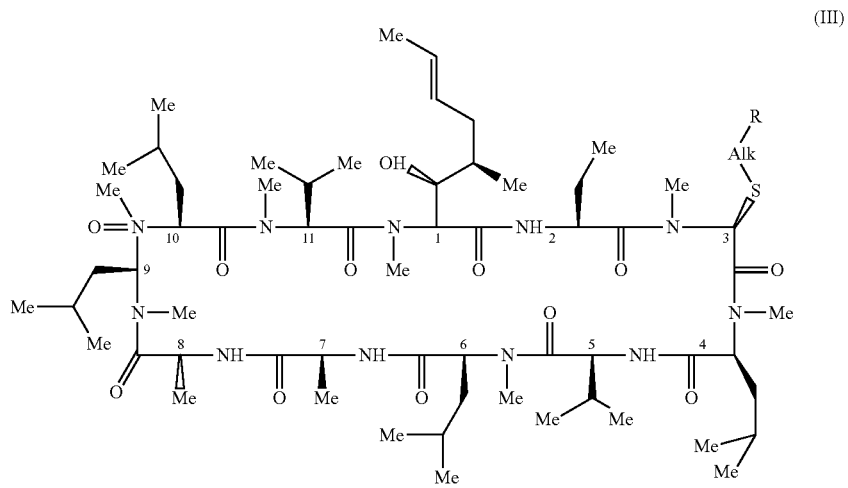

wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$, R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

The present compositions and methods may be practiced employing any suitable compositions or combinations of compositions including therapeutically effective amounts of cyclosporine component in conjunction with bimatoprost, latanoprost, latanoprost acid and travoprost and travoprost free acid useful to promote hair growth. The cyclosporine component is present in an amount and/or concentration effective enough to provide the desired therapeutic effect when the cyclosporine-containing composition is administered to a human or animal in accordance with the present invention. Mixtures of cyclosporine components are contemplated. In one embodiment of the invention, the cyclosporine component advantageously is present in the compositions in amounts ranging from about 0.01-0.05% w/v, 0.05-0.1% w/v, 0.1% to about 0.5% w/v, 0.5%-5% w/v, 5%-15% w/v, and 15% or about 20% or 25% w/v of the composition.

In another embodiment, the cyclosporine component is present in an amount of about 0.01% to about 5% or about 10% or about 15% by weight of the composition. Cyclosporine may be present in the following concentrations: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, %, 0.11%, 0.12%. 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0%, 10%, 11%, 12%, 13%, 14%, 15%, 16%, 17%, 18%, 19%, 20%, 21%, 22%, 23%, 24% and 25% w/w, w/v or v/v.

Cyclosporine, both topical and oral, in all its various forms may be present in combination with bimatoprost, latanoprost, latanoprost acid, travoprost, travoprost free acid, minoxidil, minoxidil sulphate and oral or topical finasteride.

C. Other Hair Growth Agents

1) Minoxidil:

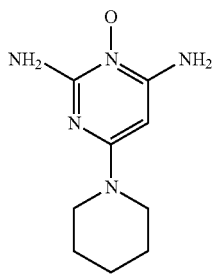

Minoxidil is believed to open adenosine triphosphate (ATP)-sensitive potassium channels and vasodilates blood vessels allowing more nutrients, blood and oxygen into the follicles. In the late telogen phase of the hair follicle growth cycle, stem cells located in the bulge region differentiate and re-enter anagen phase. In patients suffering from androgenetic alopecia hair follicles become smaller and anagen phase is shortened in duration. Minoxidil increases the amount of intracellular Ca2+, which may upregulate the enzyme adenosine triphosphate (ATP) synthase, independent of its role in ATP synthesis, and promotes stem cell differentiation. It is theorized that minoxidil induced Ca2+ influx can increase stem cell differentiation and may be a factor in the mechanism by which minoxidil facilitates hair growth (Mechanism of Action of Minoxidil in the Treatment of Androgenetic Alopecia . . . ), A. Gren et al., *J Biol Regul Homeost Agents* 31(4): 1049-1053 (2017).

There is some evidence that minoxidil may cause hair in the telogen phase to shed, which are replaced by newer and thicker hairs in the anagen phase. Minoxidil is a prodrug which converts to minoxidil sulphate by the sulfotransferase enzyme SULT1A1.

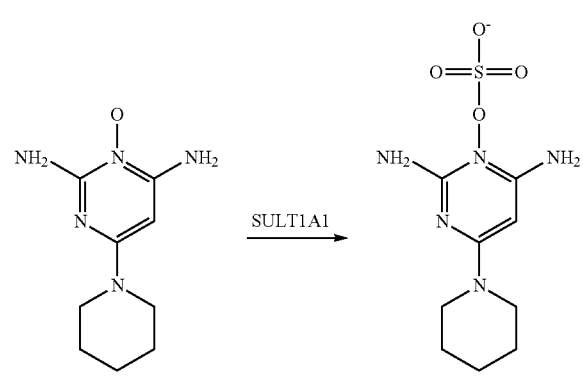

Further, minoxiddl sulphate as compared to minoxiddl is a much more potent hair growth agent. Some studies speculate that the amount of enzyme SULT1A1 in and around the hair follicles is what determines whether individuals respond well to minoxidil. Minoxidil can be combined with bimatoprost, latanoprost, 15-keto latanoprost, 15(S)-latanoprost, 5-trans latanoprost, latanoprost-d4, latanoprost lactol, latanoprost ethyl amide-d4 and latanoprost acid, travoprost and travoprost free acid which in theory causes entry into the anagen phase more quickly and lengthens the anagen phase. Minoxidil can also be combined with cyclosporine. Minoxidil can be combined with those compounds at the following concentrations: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, %, 0.11%, 0.12%, 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9, 4.0%, 4.1%, 4.2%, 4.3%, 4.4%, 4.5%, 4.6%, 4.7%, 4.8%, 4.9%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, 20%, 21%, 22%, 23%, 24% and 25% w/w, w/v or v/v.

2) Finasteride

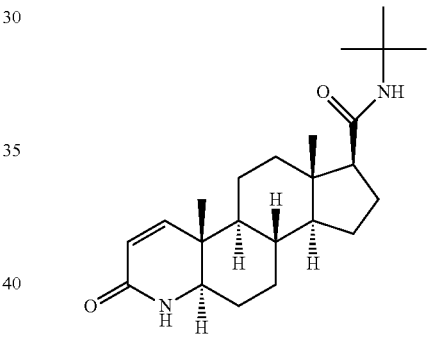

Finasteride ($C_{23}H_{36}N_2O_2$), also known as (1S,3aS,3bS,5aR,9aR,9bS,11aS)-N-tert-butyl-9a,11a-dimethyl-7-oxo-1,2,3,3a,3b,4,5,5a,6,9b,10,11-dodecahydroindeno[5,4-f]quinoline-1-carboxamide, is a 5α-reductase inhibitor originally used to treat enlarged prostates in males. Oral finasteride works by decreasing the production of dihydrotestosterone (DHT) by about 70%, including in the prostate gland and the scalp. There have been some reports of success in growing scalp hair using topical finasteride. Finasteride can be combined with the prostaglandin analogs of the present invention including bimatoprost, latanoprost and travoprost and their analogs.

Finasteride can be combined with bimatoprost, latanoprost, 15-keto latanoprost, 15(S)-latanoprost, 5-trans latanoprost, latanoprost-d4, latanoprost lactol, latanoprost ethyl amide-d4 and latanoprost acid, travoprost and travoprost acid which in theory causes entry into anagen phase more quickly and lengthens anagen phase. Finasteride can be combined with minoxidil, minoxidil sulphate or cyclosporine. Finasteride can be combined with those compounds at the following concentrations: 0.001%, 0.002%, 0.003%, 0.004%, 0.005%, 0.006%, 0.007%, 0.008%, 0.009%, 0.0.01%, 0.02%, 0.03%, 0.04%, 0.05%, 0.06%, 0.07%, 0.08%, 0.09%, 0.1%, %, 0.11%, 0.12%. 0.13%, 0.14%, 0.15%; 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, 20%, 21%, 22%, 23%, 24% and 25% w/w, w/v or v/v.

Definitions

The term "about" refers to slight variations in the concentrations of active agents or excipients that a regulatory agency such as the FDA or EMEA would find to be bioequivalent.

The term "aerosol foam" is a product, which includes a liquid foamable composition and a propellant liquid, filled into a pressurized container that is equipped with a valve system and nozzle at the top of the container, and a dip tube that runs from the valve system to the bottom of the container. When the valve is open, the pressure on the liquid propellant is instantly reduced and it starts to evaporate forming a high-pressure gas layer at the top of the container. This high-pressure gas layer pushes the liquid product, as well as some of the liquid propellant, up the dip tube and out through the nozzle. When the liquids flow through the nozzle, the liquid propellant evaporates into gas and in the process forms propellant gas bubbles in the liquid product creating foam.

An "effective amount" of a compound is an amount sufficient to contribute to the treatment, prevention, or reduction of a symptom or symptoms of a disease. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or formulation is an amount of a drug or formulation that, when administered to a subject, will have the intended prophylactic effect, e.g., preventing or delaying the onset (or reoccurrence) a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. Thus, a prophylactically effective amount may be administered in one or more administrations.

"Emulsion" refers in the customary sense to a mixture of two or more immiscible liquid components, one component (e.g., a therapeutic lipid described herein or mixture thereof including surfactant) being dispersed through the other component (e.g., the aqueous component of a composition described herein). The term "sub-micron emulsion" refers to an emulsion containing components having an extent in the longest dimension of less than about 1 micron.

"Growing hair" or "grow hair" refers to causing hair growth to increase as compared to the rate of hair growth without applying the drugs and/or formulations of the present invention.

"Hairs" may be vellus hairs which are fine, thin, non-pigmented short hairs in which the hair bulb is located superficially in the dermis. Intermediate hairs that are in a growth stage between vellus ("baby" or immature) hair, such as on your face, and mature hair stage of growth such as the hair on the scalp. Terminal hairs are coarse, pigmented, long hairs in which the bulb of the hair follicle is seated deep in the dermis. As alopecia progresses, a transition takes place in the area of approaching baldness wherein the hairs themselves are changing from the terminal to the vellus type.

"Hair loss" may refer to alopecia areata, androgenetic alopecia, male pattern hair loss, female pattern hair loss, telogen effluvium, anagen effluvium, tinea capitis, cicatricial alopecia, lichen planopilaris, discoid lupus erythematsus, folliculitis decalvans, dissecting cellulitis of the scalp, central centrifugal cicatricial alopecia, frontal fibrosing alopecia, loose anagen syndrome, hair shaft abnormalities, involutional alopecia, androgenic alopecia, trichotillomania, hair loss due to chemotherapy, hair loss due to infectious agents, trichorrhexis *nodosa* and senescent alopecia.

"Locale of hair follicles" means an area of skin (scalp, brow, eyelid margins, face, etc.) containing hair follicles.

"Non-aerosol, non-spray foam" is a product, which comprises a foamable liquid composition, which is filled into a non-pressurized container that is equipped with a mechanical pump, an air chamber, a mixing chamber, a foam forming screen mesh, and a dip tube that runs from the mechanical pump to the bottom of the container. When the mechanical pump is actuated, the foamable liquid composition is forced up the dip tube into the mixing chamber where it is comingled with air from the air chamber, at a predetermined ratio to form foam. It is the actuation of the pump that pressurizes and causes the turbulent comingling of the air and the liquid foamable composition to form air bubbles in the foamable liquid composition creating foam. From the mixing chamber, the foam is then homogenized into fine uniform bubbles when it passes through the screen mesh before being dispensed out through the nozzle. Therefore, it is a non-propellant method of propelling the liquid product out of the container in the form of foam. A major difference in the continuous state of the containers is that in an aerosol foam container the propellant fluid (typically compressed gas or liquefied gas) is pumped into the container under high pressure after the container is sealed and is maintained continuously in pressurized state, whereas in stark contrast in the container of the non-aerosol, non-spray foam, the air inside the container is constantly under atmospheric pressure.

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. See e.g., Berge et al., "Pharmaceutical Salts", *Journal of Pharmaceutical Science*, 1977, 66, 1-19). Additional information on suitable pharmaceutically acceptable salts can be found in REMINGTON'S PHARMACEUTICAL SCIENCES, 17th ed., Mack Publishing Company, Easton, Pa., 1985, which is incorporated herein by reference. Certain specific compounds of the present invention contain both basic and acidic functionalities that allow the compounds to be converted into either base or acid addition salts.

"Preventing hair loss" means slowing down or preventing hair loss that would occur as compared to if a formulation of the present invention was not applied.

The methods and compositions of the present invention of the present invention can be used to prevent hair loss, to treat hair loss, to treat or thicken thinning hair, to treat loss of eyebrows, to treat loss of eyelashes or facial hair, and can be used to treat all types of alopecia, convert vellus hair to terminal hair or increase melanin content in hair by turning the hair darker or increasing the ratio of dark hair to grey hair on the scalp, eyebrows, eyelashes or facial hair.

The term "prodrug" is used according to its plain ordinary meaning and is intended to mean compounds that require a chemical or enzymatic transformation in order to release the active parent drug in vivo prior to producing a pharmacological effect.

The term "soluble" refers the ability of the solvent to dissolve an amount of the active pharmaceutical ingredient that is relevant for its pharmacological effect.

The terms "solvent" and "solvent system" define one component of the formulation, the liquid or semi-solid phase that contains the API.

The terms "stable" and "stability" are used here in relation to the shelf-life of a pharmaceutical product, and are related to the physical change, degradation or chemical decomposition of active pharmaceutical ingredients or formulation, which limits the shelf-life of a product.

"Synergism" between two drugs, for example in a fixed combination, can occur when the two drugs interact in a manner that enhance or magnify one or more effects, or with two different mechanisms of actions which when combined result in a greater therapeutic affect or efficacy than either drug applied alone or the two drugs serially, or avoid or lower unwanted side effects when the drugs are provided as monotherapies, of those drugs. Negative effects of synergy are a form of contraindication such as when more than one depressant drug is used that affects the central nervous system (CNS), an example being alcohol and Valium. "Synergism" has also been noted in describing how complex systems operate. For example, biological systems may react in a non-linear way to perturbations, so that the outcome may be greater than the sum of the individual component alterations.

In describing the present invention, synergism means that the combination of the two active drugs, utilized in the methods and compositions of the invention achieves a result, e.g. stimulating the growth of hair such as scalp hair, eyebrows or eyelashes, in a mammal, e.g. a human, that is greater than the result achieved when the active drugs are utilized, alone as monotherapies, under the same conditions. Thus, to determine the combinations that are within the scope of the present invention, one may simply compare the result achieved by the combination of the two drugs with the result achieved with each of the individual drugs, alone.

The term "topical" in the context of methods described herein relates in the customary sense to the administration of a compound or pharmaceutical composition which is incorporated into a suitable pharmaceutical carrier and administered at a topical treatment site of a subject. Accordingly, the term "topical pharmaceutical composition" includes those pharmaceutical forms in which the compound is administered externally by direct contact with a topical treatment site, e.g., the skin, scalp, brow, eyelid margins, face. The term "topical epidermal pharmaceutical composition" refers to a pharmaceutical composition suitable for administering directed to the epidermal layer of the skin, e.g., the palpebra, the supercilium, the scalp, or the body. The term "topically administering" refers to administering externally by direct contact with a topical treatment site. The term "topical epidermal administering" refers to administering externally by direct contact with the epidermis.

The terms "treat" "treating" or "treatment" may refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or computerized imaging systems. For example, the certain methods presented herein successfully treat hair loss by decreasing the incidence of hair loss, in inhibiting its symptoms and or cause and causing new hair growth.

Anatomy of Hair and Hair Growth

Orifices of hair follicles occupy only about 0.1% of the total skin surface area of humans, while hair follicles can occupy as much as 10% of the total surface area on the human scalp (Schaefer, H., et. al. (1990) "Follicular penetration" (pgs. 163-173)(1990). In general, follicular openings lead to epithelial surfaces that do not have the protective stratum corneum of surface skin. Consequently, hair follicles and sebaceous glands contribute significantly to transdermal drug delivery. Consequently, hydrophilic drugs can penetrate with high flux and usually through the intrafollicular routes, along the junction of the internal and external route sheath, and rapid diffusion into the dermis by the outer route sheath. Longer lag times for the scalp skin penetration of hydrophilic drugs, as compared to the shorter time for lipophilic drugs, suggest that the permeation of hydrophilic drugs via the upper dermis is a rate-limiting step. The penetration routes of lipophilic drugs is probably along the junction of internal and external root sheath.

Release of sebum by sebaceous glands associated with the hair follicle forms a lipoidal pathway for lipophilic materials in the follicles (Ebling et al., 1991).

It is also believed that a penetration route for lipophilic permeants is the transepidermal pathway. Thus, the penetration through the stratum corneum of scalp skin is also an important pathway but some drugs may use the trans follicular route. Sebum located in the follicles also plays an important role in drug penetration in the outer root sheath. Human hair follicles can vary in diameter from 5 um to 80 um, which can affect trans-follicular penetration.

Certain penetration enhancers and solvents help fluidize lipids, in intercellular channels of the stratum corneum. Penetration of permeants and drugs through the scalp skin, is believed to be related to the rapid permeation into the hair follicles and the rapid diffusion through the outer root sheath, into the dermis, whereas the trans epidermal permeation of drugs is largely via the microchannels. Hydrophilic drugs also rapidly diffused into the dermis via the outer root sheath, but permeation of hydrophilic drugs via the upper dermis may be rate-limiting step and relatively slow.

Human scalp anagen hair follicles are believed to express the genes and protein for prostanoid receptors in the dermal papillae and the CTS surrounding the hair bulb, but not in the epithelial keratinocytes or the melanocytes of the hair bulb. One theory is that some prostaglandin analogues bind to specific receptors on the plasma membrane of cells in the regulatory dermal papilla in the hair bulb, which probably stimulates intracellular signaling pathways, resulting in hair growth and the lessening of hair loss. For example, although not wishing to be bound to any theory, prostaglandin analogs such as latanoprost may increase the number of hairs in the anagen phase by shifting hairs from the resting telogen phase to the anagen phase, shortening the time to begin the anagen phase and lengthening the anagen phase, which causes hair to grow longer. In patients suffering from androgenetic alopecia, the anagen phase is reduced in duration and follicles spend more time in the telogen phase as compared to patients not suffering from androgenetic alopecia. Latanoprost, travoprost and bimatoprost, in varying degrees, may also stimulate melanogenesis in melanocytes and keratogenesis found in the dermal papilla which results in darker hair, with more melanin expressed in the individual hair and also increases the individual hair diameter and the size of the dermal papilla, which in turn results in an increase in number of hairs which are longer, darker and thicker than hairs would be if not being treated with latanoprost, travoprost and bimatoprost. And while it has been reported that bimatoprost may induce certain signals in the dermal papilla which accounts for its use in growing eyelashes, bimatoprost, which is a prostamide, is believed to have a separate receptor system from prostaglandin analogs and therefore a differing mechanism of action (Khidir, "The Prostamide-related glaucoma therapy . . . " FASEB, 27[2]: 557-567 [February 2013]).

Keratinocyte cells are found in the outermost layer of the skin known as the epidermis. Keratinocyte cells are also found in the basal layer of skin. Keratinocyte cells make up about 95% of the epidermis. Keratinocytes undergo keratinization and form the superficial layer of skin. These superficial keratinized cells are continuously replaced by cells derived from mitotic cells in the lowest layer of the epidermis which is the basal layer. The cells in the basal layer are sometimes called basal keratinocytes or basal cells. The epidermis is about 0.2 mm thick. Inside the epidermis, keratinocytes are arranged in four different layers known as the stratum basale, stratum spinosum, stratum granulosum, and stratum corneum. Melanocytes located in the basal layer do not undergo keratinization but produce melanin. Melanin accumulates in small granules known as melanosomes which are transported to dendrites and then transferred to keratinocytes. Keratinocytes and melanocytes are located in hair follicles along with dermal fibroblasts. Homeostasis of the epidermis and hair follicle is primarily regulated by the cellular interaction between keratinocytes and melanocytes. Keratinocytes stimulate melanocyte functions such as melanogenesis, proliferation, differentiation and dendritogenesis through paracrine signaling from cell to cell. Hirobe, "Keratinocytes Regulate the Function of Melanocytes" *Dermatolgica Sinica*. Vol. 32, pgs. 200-204 (2014). It is theorized that prostaglandin analogs such as latanoprost or travoprost may act on keratinocytes, which make hair, and melanocytes which produce pigment. It is possible that prostaglandin analogs act directly upon keratinocytes to make individual hairs thicker in diameter and melanocytes to make hair the hair darker or rather, the normal hair color of the individual user. It is also possible that this occurs through indirect action via the dermal papilla, which is located at the center of the hair bulb at the follicular base, by paracrine signals to the keratinocytes and/or melanocytes which is a result of an undefined follicular signaling system.

Eyebrows

Loss of eyebrow hair, also known as madarosis, is characterized by a lack of growth or loss of eyebrow hair. Loss of eyebrow hair can have cosmetic, functional, and social/psychological consequences. According to the research, the diameter of scalp hair is normally thicker than eyebrow hair in Asian patients, while the reverse is true in Caucasian patients (Gandelman M. A Technique for Reconstruction of Eyebrows and Eyelashes. *Semin Plast Surg*. 19:153-8 (2005)). Eyebrow hair is generally less dense laterally than medially which results in hair loss in the eyebrows and brings more noticeable in the lateral portion. Eyebrows can be roughly divided into three areas. The medial third is usually below the orbital margin with the hairs in this region oriented vertically. The middle third lies along the orbital margin with hairs oriented obliquely or horizontally. The lateral third usually lies above the orbital margin.

Madarosis of the eyebrows can be caused by disease such as dermatological diseases, endocrinopathy, such as thyroid disease and due to psychological disorders such as trichotillomania and chemotherapy. Heredity can also play a factor in conditions such as congenital aplasia. Madarosis of the eyebrows can by physical trauma such as burns, complications with cosmetic procedures such tattooing and complications from implantation.

Eyelashes

Eyelashes serve a functional and protective mechanism by protecting the eye by keeping foreign particles and objects from entering the eye. Long eyelashes are considered generally to be more attractive than short eyelashes across most cultures. The nervous system surrounding the eye is more easily excited to protect the eyes in most mammals. Loss of eyelashes is known as hypotrichosis of the eyelashes which includes idiopathic hypotrichosis, chemotherapy induced hypotrichosis, alopecia areata and hypothyroidism. Eyelash length is largely proportional to age with younger people having longer eyelashes and older people having shorter eyelashes. Current treatment for hypotrichosis of the eyelashes includes LATISSE® which is a 0.03% w/v bimatoprost solution and is applied to the upper eyelid margin.

Chemotherapy

Chemotherapy induced alopecia occurs mainly because the chemotherapeutic agent damages the hair follicle resulting in total or incomplete hair loss. Hair loss occurs in approximately 65% of chemotherapeutic patients. Loss of hair is generally all over the body and is not limited to the scalp and include eyelashes and eyebrows. Hair loss due to chemotherapy can be psychologically devastating and has been described by some patients as a constant reminder of their illness and can result in feelings of loss of control and increased social isolation (Beisecker, Analee et al., *Side Effects of Adjuvant Chemotherapy*, Pycho-Oncology, 1997, 83-93-6). Focus groups have also demonstrated that the loss of eyelashes and eyebrow hair was psychologically more devastating than loss of scalp hair.

Other non-chemotherapy drugs can also cause hair loss such as anticoagulants, oral contraceptives, retinoids, anti-thyroid drugs and interferons. Generally, chemotherapy-induced hair loss results from toxicity to rapidly dividing cells in the hair follicle. During anagen, the epithelial compartment of the hair follicle undergoes rapid proliferation, with the greatest proliferation in the bulb matrix cells. When chemotherapeutic agents are administered to a patient, cell mitosis can abruptly stop resulting in hair loss because the partially keratinized hair shaft weakens and leads to the hair falling out. This is known as anagen effluvium. Chemotherapeutic agents can also cause apoptosis (programmed cell death) to cells in the hair follicle. In general, when chemotherapy is ended, hair growth returns but in some patients it can take years or several complete hair cycles to achieve the same level of hair growth the patient was experiencing prior to chemotherapy. Generally, the new hair is vellus hair rather than terminal hair. The formulations and methods described in the specification can be used before or during chemotherapy on the scalp, face, eyebrows, eyelashes and all over the body to prevent loss of hair and also after chemotherapy to regrow hair and shift the hair cycle into anagen phase and lengthens anagen phase resulting in longer, darker and thicker eyelashes, eyebrows, scalp hair and facial hair.

Vehicles

TABLE 1 list solvents and penetration enhancers:

| | | |
|---|---|---|
| Capmul 808G EP/NF | Glyceryl Monocaprylate | 26402-26-6 |
| Capmul GDB EP/NF* | Glyceryl Dibehenate | 94201-62-4 |
| Capmul GMO-50 EP/NF | Glyceryl Monooleate | 25496-72-4 |
| Capmul MCM C8 EP/NF | Glyceryl Monocaprylate | 26402-26-6 |
| Capmul MCM EP/NF | Glyceryl Caprylate/Caprate | 91744-32-0, or 26402-22-2, and 26402-26-6 |
| Capmul INJ MCM EP/NF | Glyceryl Caprylate/Caprate | 91744-32-0, or 26402-22-2 and 26402-26-6 |
| CAPMUL INJ MCM EP | Glyceryl Caprylate/Caprate | 91744-32-0, or 26402-22-2, and 26402-26-6 |
| Capmul PG-2L EP/NF | Propylene Glycol Dilaurate | 22788-19-8 |
| Capmul PG-8 NF | Propylene Glycol Monocaprylate | 68332-79-6, or 31565-12-5 |
| Capmul PG-8-70 NF | Propylene Glycol Monocaprylate, NF Type 1 | 68332-79-6 |
| Capmul PG-12 EP/NF | Propylene Glycol Monolaurate | 27194-74-7 |
| CAPTEX ® 170 EP | Coco-Caprylate/Caprate | 95912-86-0 |
| CAPTEX 200P | Propylene Glycol Dicaprylocaprate | 68583-51-7 |
| CAPTEX 300 EP/NF | Glyceryl Tricaprylate/Tricaprate | 65381-09-1 |
| CAPTEX INJ 300 LOW C6 EP/NF/JPE | Glyceryl Tricaprylate/Tricaprate | 65381-09-1, or 73398-61-5 |
| CAPTEX 355 EP/NF/JPE | Glyceryl Tricaprylate/Tricaprate | 65381-09-1, or 73398-61-5 |
| CAPTEX INJ 355 EP/NF/JPE | Glyceryl Tricaprylate/Tricaprate | 65381-09-1, or 73398-61-5 |
| CAPTEX 8000 | Glyceryl Tricaprylate, Tricaprylin | 538-23-8 |
| CAPTEX INJ 8000 NP | Glyceryl Tricaprylate, Tricaprylin | 538-23-8 |
| Captex 100 | Propylene Glycol Dicaprate | 53824-77-4 |
| Captex 170 | Caprylic/Capric Acid Ester of Saturated Fatty Alcohol C12-C18 | 95912-86-0 |
| Captex GTO | Triolein | 122-32-7 |
| Captex NPGC | Decanoic acid, mixed esters with neopentyl glycol and octanoic acid | |
| CAPTEX INJ 300 LOW C6 EP/NF/JPE | Glyceryl Tricaprylate/Tricaprate | 65381-09-1, or 73398-61-5 |
| CAPTEX INJ 355 EP/NF/JPE | Glyceryl Tricaprylate/Tricaprate | 65381-09-1, or 73398-61-5 |
| CAPTEX INJ 8000 NP | Glyceryl Tricaprylate, Tricaprylin | 538-23-8 |
| Capmul INJ MCM EP* | Caprylic capric mono- & diglycerides | 91744-32-0, or 26402-22-2, and 26402-26-6 |
| Acconon INJ MC8-2 EP/NF* | PEG-8 caprylic/capric glycerides | 91744-32-0, 223129-75-7 |
| CremerCOOR ® MCT 60-40 | Caprylic/Capric Triglyceride | 65381-09-1 |
| CremerCOOR ® MCT 70-30 | Caprylic/Capric Triglyceride | 65381-09-1 |
| CremerCOOR ® EHC | 2-Ethylhexyl Cocoate | 92044-87-6 |
| CremerCOOR ® EHL | 2-Ethylhexyl Laurate | 20292-08-4 |
| CremerCOOR ® EHP | 2-Ethylhexyl Palmitate | 29806-73-3 |
| CremerCOOR ® EHS | 2-Ethylhexyl Stearate | 91031-48-0 |
| CremerCOOR ® GMS 40/SE (self-emulsifier) | Glycerol stearate | 67701-33-1 |
| CremerCOOR ® IPM | Isopropyl Myristate | 110-27-0 |
| CremerCOOR ® IPP | Isopropyl Palmitate | 142-91-6 |

TABLE 1-continued list solvents and penetration enhancers:

| CremerCOOR® Triacetin | Glycerol Triacetate | 102-76-1 |
| | 1,2-DIMYRISTOYL-SN-GLYCERO-3-PHOSPHOCHOLINE | 18194246 |
| | DIISOPROPANOLAMINE | 110974 |
| | DIISOPROPYL ADIPATE | 6938949 |
| | DIPROPYLENE GLYCOL FATTY ACID ESTERS (Medium and short chain) | 25265718 |
| | MYRISTYL ALCOHOL | 112721 |
| | N,N-DIMETHYLACETAMIDE | 127195 |
| | POLYOXYL 35 CASTOR OIL | 61791126 |
| | POLYOXYL 40 STEARATE | 9004993 |
| | POLYOXYL 40 HYDROGENATED CASTOR OIL | 61788850 |

The solvents and penetration enhancers may be present in the following concentrations: 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0%, 10% w/w, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% w/w, w/v or v/v of the formulation.

Carbomer may be at a concentration of about 0.05-3.0% w/w, isopropyl myristate at a concentration of about 0.1 to about 10% w/w; PEG 40 castor oil at a concentration of about 0.1 to 20% w/w; carboxymethyl cellulose from 0.1-5.0% w/w ethanol about 1 to about 70% w/w; diethylene glycol monoethyl ether at a concentration of about 1.0 to about 50% w/w; polysorbate 20 at a concentration of about 0.1 to about 5.0% w/w; polysorbate 40 at a concentration of about 0.1 to about 5.0% w/w; polysorbate 60 at a concentration of about 0.1 to about 5.0% w/w; glycerin at a concentration of about 1.0 to about 30% w/w; polysorbate 80 at a concentration of about 0.1 to about 5.0% w/w; PPG-5 ceteth-20 at a concentration of about 0.1 to about 5.0% w/w; oleic acid at a concentration of about 0.1 to about 5.0% w/w; isostearyl isostearate at a concentration of about 0.1 to about 10% w/w; dipropylene glycol dimethyl ether at a concentration of about 1 to about 50% w/w; diethylene glycol at a concentration of about 1 to about 50% w/w; dipropylene glycol at a concentration of about 1 to about 50% w/w; caprylic/capric at a concentration of about 0.1 to about 10% w/w; benzyl alcohol at a concentration of about 0.1 to about 2.0% w/w; silicone at a concentration of about 0.1 to about 10% w/w; PEG 40 castor oil at a concentration of about 0.1 to 20% w/w; PEG 35 castor oil at a concentration of about 0.1 to 20% w/w; oleyl alcohol at a concentration of about 0.1 to 10% w/w; glyceryl monooleate at a concentration of about 0.1 to 10% w/w; and/or water at a concentration of about 0 to about 90% w/w.

EXAMPLES

Formulation I
0.05% w/v latanoprost;
0.06% w/v cyclosporine A;
10.0% w/v diethylene glycol monoethyl ether;
5.0% w/v oleyl alcohol; and,
q.s. water 100%.
Formulation II
0.08% w/v latanoprost;
0.1% w/v cyclosporine A;
15.0% w/v diethylene glycol monoethyl ether;
5% w/v PEG;
6.0% w/v oleyl alcohol; and,
q.s. water 100%.
Formulation III
0.08% w/v latanoprost;
0.1% w/v cyclosporine A;
15.0% w/v diethylene glycol monoethyl ether;
5% w/v PEG;
6.0% w/v oleyl alcohol; and,
q.s. water 100%.
Formulation IV
0.06% w/v bimatoprost;
0.08% w/v cyclosporine A;
10.0% w/v glyceryl monooleate;
5.0% w/v oleic acid;
5% w/v ethanol; and,
q.s. water 100%.
Formulation V
0.08% w/v bimatoprost;
0.1% w/v cyclosporine A;
10.0% w/v diethylene glycol monoethyl ether;
5.0% w/v oleic acid;
5.0% w/v oleyl alcohol; and,
q.s. water 100%.
Formulation VI
0.08% w/v latanoprost or latanoprost acid;
0.08% w/v cyclosporine A;
10.0% w/v polyethylene glycol;
10.0% w/v diethylene glycol monoethyl ether;
5.0% w/v oleyl alcohol; and,
q.s. water 100%.
Formulation VII
0.05% w/v bimatoprost;
0.07% w/v cyclosporine A;
10.0% w/v oleyl alcohol;
10.0% w/v diethylene glycol monoethyl ether; and,
q.s. water 100%.

Formulation VIII
0.05% w/v latanoprost or latanoprost acid;
0.08% w/v cyclosporine A;
5.0% w/v diethylene glycol monoethyl ether;
10.0% w/v CAPTEX 300 EP/NF;
10.0% w/v PEG; and,
q.s. water 100%.
Formulation IX
0.06% w/v uenoprostone isopropyl ester free acid;
0.08% w/v cyclosporine A;
5.0% w/v diethylene glycol monoethyl ether;
10.0% w/v CAPTEX 300 EP/NF;
10.0% w/v PEG; and,
q.s. water 100%.
Formulation X
0.07% w/v travoprost or travoprost free acid;
0.08% w/v cyclosporine A;
5.0% w/v diethylene glycol monoethyl ether;
10.0% w/v CAPTEX 300 EP/NF;
10.0% w/v PEG; and,
q.s. water 100%.
Formulation XI
0.1% w/v bimatoprost;
005% w/v cyclosporine A;
20% w/v 2-(2-Ethoxyethoxy)-Ethanol;
5% w/v propanediol;
3% w/v oleic acid; and,
q.s. water 100%.
Formulation XII
0.1% w/v latanoprost;
005% w/v cyclosporine A;
20% w/v 2-(2-Ethoxyethoxy)-Ethanol;
5% w/v propanediol;
3% w/v oleic acid; and
q.s. water 100%.
Formulation XIII
0.1% w/v latanoprost;
5.0% w/v minoxidil;
10% w/v 2-(2-Ethoxyethoxy)-Ethanol;
5% w/v propanediol;
3% w/v oleic acid; and,
q.s. water 100%.
Formulation XIV
0.1% w/v latanoprost;
5.0% w/v minoxidil or minoxidil sulphate;
20% w/v 2-(2-Ethoxyethoxy)-Ethanol;
5% w/v propanediol;
3% w/v oleic acid; and,
q.s. water 100%.
Formulation XV
0.1% w/v latanoprost;
2.0% w/v minoxidil or minoxidil sulphate;
20% w/v 2-(2-Ethoxyethoxy)-Ethanol;
5% w/v propanediol;
3% w/v oleic acid; and,
q.s. water 100%.
Formulation XVI
0.1% w/v bimatoprost;
5.0% w/v minoxidil;
20% w/v 2-(2-Ethoxyethoxy)-Ethanol;
5% w/v propanediol;
3% w/v oleic acid; and,
q.s. water 100%.
Formulation XVII
0.1% w/v travoprost;
5.0% w/v minoxidil;
20% w/v 2-(2-Ethoxyethoxy)-Ethanol;
5% w/v propanediol;
3% w/v oleic acid; and,
q.s. water 100%.
Formulation XVIII
0.1% w/v latanoprost;
5.0% w/v minoxidil;
30.0% w/v ethanol;
50% w/v propylene glycol; and,
q.s. water 100%.
Formulation XVIIII
0.1% w/v latanoprost;
5.0% w/v minoxidil;
30.0% w/v ethanol;
50% w/v propylene glycol;
3% w/v diethylene glycol monoethyl ether;
2% w/v oleyl alcohol; and,
q.s. water 100%.
Formulation XX
0.3% w/v latanoprost;
5.0% w/v minoxidil;
30.0% w/v ethanol;
50% w/v propylene glycol; and,
q.s. water 100%.
Formulation XXI
5.0% w/v minoxidil or minoxidil sulphate;
0.05% w/v latanoprost;
30.0% w/v ethanol;
50% w/v propylene glycol; and,
q.s. water 100%.
Formulation XXII
5.0% w/v minoxidil;
0.05% w/v latanoprost;
30.0% w/v ethanol;
50% w/v propylene glycol; and,
q.s. water 100%.
Formulation XXIII
5.0% w/v minoxidil;
0.008% w/v latanoprost;
30.0% w/v ethanol;
50% w/v propylene glycol;
q.s. water.
Formulation XXIV
5.0% w/v minoxidil;
0.007% w/v latanoprost;
30.0% w/v ethanol;
50% w/v propylene glycol; and,
q.s. water 100%.
Formulation XXV
5.0% w/v minoxidil;
0.005% w/v latanoprost;
30.0% w/v ethanol;
50% w/v propylene glycol; and,
q.s. water 100%.
Formulation XXVI
3.0% w/v finasteride;
0.1% w/v latanoprost;
30.0% w/v ethanol;
50% w/v propylene glycol; and,
q.s. water 100%
Formulation XXVII
5.0% w/v finasteride;
0.3% w/v latanoprost;
30.0% w/v ethanol;
50% w/v propylene glycol; and,
q.s. water 100%.
Formulation XXVIII
5.0% w/v finasteride;

0.3% w/v bimatoprost;
30.0% w/v ethanol;
50% w/v propylene glycol; and,
q.s. water 100%.
Formulation XXVIIII
5.0% w/v finasteride;
0.1% w/v bimatoprost;
30.0% w/v ethanol;
50% w/v propylene glycol; and,
q.s. water 100%.
Formulation XXX
5.0% w/v finasteride;
0.1% w/v travoprost;
30.0% w/v ethanol;
50% w/v propylene glycol; and,
q.s. water 100%.
Formulation XXXI
5.0% w/v finasteride;
0.3% w/v travoprost;
30.0% w/v ethanol;
50% w/v propylene glycol; and,
q.s. water 100%.
Formulation XXXII
0.1% w/v latanoprost;
47% w/v ethanol;
0.4% w/v polysorbate 60;
1% w/v polyethylene lauryl alcohol;
0.3% w/v acetic acid;
10% w/v propylene glycol; and,
q.s. water 100%.
Formulation XXXIII
0.3% w/v latanoprost;
47% w/v ethanol;
0.4% w/v polysorbate 60;
1% w/v polyethylene lauryl alcohol;
0.3% w/v acetic acid;
10% w/v propylene glycol; and,
q.s. water 100%.
Formulation XXXIV
0.08% w/v latanoprost;
4.0% w/v minoxidil;
50% w/v propylene glycol;
30% w/v ethanol;
3% w/v transcutol;
2% w/v oleyl alcohol;
0.5% w/v POE 40; and,
q.s. water 100%.
Formulation XXXV
0.08% w/v latanoprost;
4.0% w/v minoxidil;
50% w/v propylene glycol;
30% w/v ethanol;
3% w/v transcutol;
2% w/v oleyl alcohol; and,
q.s. water 100%.
Formulation XXXVI
0.1% w/v latanoprost;
47% w/v ethanol;
0.4% w/v polysorbate 60;
1% w/v polyethylene lauryl alcohol;
0.3% w/v acetic acid;
2.0% w/v oleic acid;
10% w/v propylene glycol; and,
q.s. water 100%.

Non-Aerosol. Non-Spray Foam Pump and Container

In another embodiment, a final product of a liquid formulation comprising the active ingredient combination of bimatoprost/minoxidil or travoprost/minoxidil or latanoprost/minoxidil or bimatoprost/finasteride or travoprost/finasteride or latanoprost/finasteride or a pharmaceutically acceptable salt thereof, packaged in a non-pressurized container, is dispensed using a non-aerosol, non-spray foam pump. The non-aerosol, non-spray foam pump provides for safe and simple dispensing of a measured dosage of the foam that contains the liquid formulation comprising the drug combination or a salt thereof, that is readily applied to the scalp, eyebrows, eyelashes or face. The non-aerosol, non-spray foam pump is calibrated to deliver an adequate volume of the foam. An additional object herein disclosed is to provide the liquid formulation in a reusable and non-pressurized container that can be manufactured in a cylindrical or non-cylindrical shapes and that contains no propellant. Therefore, the present embodiment does not employ the use of pressurized containers containing typical propellants, such as liquefied petroleum gases (mixture of propane, isobutene, and n-butane), chlorofluorocarbons (CFCs), and dimethyl ether, which are flammable, harmful, and toxic volatile organic compounds (VOCs). The present embodiment is safely transported, stored, and dispensed in reusable containers. Reusing products and the parts of products is extremely important for the environment.

Foam Formulations

Foam formulations comprising the active ingredient combination of bimatoprost/minoxidil or travoprost/minoxidil or latanoprost/minoxidil or bimatoprost/finasteride or travoprost/finasteride or latanoprost/finasteride or a pharmaceutically acceptable salt thereof. Preferably the amount of surfactant is about 2-10%. Any combination of anionic, cationic, non-ionic or amphoteric surfactants and non-ionic block copolymers may be used. Preferably ethoxylated glycerides, ethoxylated sorbitan esters, polyethoxylated and/or hydrogenated castor oil, nonionic block copolymers and amphoteric surfactants may be used. Especially preferred surfactants may be selected from: PEG 40 hydrogenated castor oil; PEG 40 Stearate; Polysorbate 20; Cocamidopropyl betaine; Glyceryl cocoate; PEG 6 caprylic/capric glycerides; Poloxamer F 68; and saturated phospholipids C6 to C10.

Formulation XXXVII (Spray Solution)
Minoxidil 5.0% w/v (active);
Latanoprost 0.1% w/v or 0.3% w/v (active);
1,2-Propanediol 60.5% w/v (solvent);
Ethyl alcohol 10.2% w/v (solvent);
lactic acid 2.5% w/v (acidifying agent);
Essence 0.06% w/v (aroma/essence); and
deionized water q.s. 100% (solvent).

The production flow scheme for formulation XXXVI I is as follows: 1: Minoxidil, latanoprost and other excipients are separately weighed and prepared; 2: 1,2-propanediol, lactic acid, ethyl alcohol and deionized water which have been respectively weighed are placed in a production vessel and are mixed for at least 5 minutes, 3: The previously weighed minoxidil is placed in a stainless steel production vessel and is mixed for at least 15 minutes in order to be dissolved, followed by the addition of the previously weighed latanoprost (in a preweighed syringe to ensure proper transfer of the oil)4: Essence is added and mixed; 5: Filling is carried out at target volume and the end product is packaged and boxed.

Formulation XXXVIII; Minoxidil 2/latanoprost 0.1 Spray
Minoxidil 2% w/v (active);
Latanoprost 0.1% w/v or 0.3% w/v (active);
1,2-Propanediol 65.9% w/v (solvent/excipient);
Ethyl Alcohol 5.2% w/v (solvent);

Lactic Acid 2.5% w/v (acidifying agent);
Essence 0.06% w/v (aroma/essence); and,
Deionized water q.s. (solvent).
The production flow scheme of the formulation is the same as Formulation XXXVII.
Formulation XXXIX: minoxidil 5/latanoprost 0.1 or 0.3 Foam
Minoxidil 5.0% w/v (active);
Latanoprost 0.1% w/v or 0.3% w/v (active);
1,2-Propanediol 51.5% w/v (solvent/excipient);
PEG 20 Oleyl Ether 0.5% w/v (surface active agent);
Plantacare 1200*10.5% w/v (surface active agent);
Komperlan KD**3% w/v (surface active agent);
Ethyl alcohol 5.2% w/v (solvent) (EP);
Lactic Acid 2.4% w/v (acidifying agent) (EP);
Essence 0.06% w/v (Aroma/Essence [EP]); and,
Deionized water 21.8% Solvent (EP).
*Lauryl glycoside
**Cocamide DEA=Coconut fatty Acid Diethanolamine
The production flow scheme of the formulation is as follows:
minoxidil, latanoprost and other excipients are separately weighed and prepared, 1,2-propanediol, lactic acid, ethyl alcohol and deionized water which have been respectively weighed are placed in a production vessel and are mixed for at least 5 minutes, the previously weighed minoxidil is placed in a stainless steel production vessel and is mixed for at least 15 minutes in order to be dissolved, followed by the addition of the previously weighed latanoprost. The previously weighed PEG 20 oleyl ether, plantacare 1200 and komperlan KD is added in a stainless steel production vessel and dissolved, essence is added and mixed. Filling is carried out at target volume and the end product is packaged and boxed.
Formulation XXXX: minoxidil 2.0%/latanoprost 0.1% Foam
Minoxidil 2% w/v;
Latanoprost 0.1% w/v or 0.3% w/v;
1,2-Propanediol 51.% w/v (solvent/excipient);
PEG 20 Oleyl Ether 0.5% w/v (surface active agent);
Plantacare 1200 10.5% w/v (surface active agent);
Komperlan KD 3% w/v (surface active agent);
Ethyl Alcohol 5.2% w/v (solvent);
Lactic Acid 2.4% w/v (acidifying agent);
Essence 0.06% w/v 9 w/v (Aroma/Essence); and,
q.s. deionized water.
Formulation XXXXI (Lotion)
Minoxidil 5% w/v;
Latanoprost 0.1% or 0.3% w/v;
Ethanol 60.3% w/v;
Polysorbate 60 0.4% w/v;
Polyoxyethylene lauryl alcohol 1.00% w/v;
Acetic Acid 0.6% w/v; and,
Purified Water to total 100%.
The apparent pH of the final formulated solution should be 6.24.
Formulation XXXXII
Minoxidil 5% w/v;
Latanoprost 0.1% or 0.3% w/v;
Cetyl Alcohol 2.20% % w/v;
Stearyl Alcohol 1.00% w/v;
Ethanol 51.8% w/v;
Polysorbate 60 0.4% w/v;
Polyoxyethylene lauryl alcohol 1.00% % w/v;
Propylene Glycol 5.00% % w/v;
Propellant P75 4.30% % w/v;
Acetic Acid q.s. pH 6.0; and,
Purified water to total 100%.
Formulation XXXXIII (Lotion)
Minoxidil 8% w/v;
Latanoprost 0.3% or 0.1% w/v;
Ethanol 50.5% w/v;
Polysorbate 60 0.4% w/v;
Polyoxyethylene lauryl alcohol 1.00% w/v;
Acetic Acid q.s. pH 6.0;
Propylene Glycol 7.3% w/v;
Benzyl Alcohol 5% w/v; and,
Purified Water to total 100%.
Formulation XXXXIV (Solution)
Latanoprost 0.1%, 0.2%, or 0.3% w/v;
Minoxidil 5% w/v;
Ethanol 51% w/v;
Polysorbate 60 0.4% w/v;
Laureth-12 1% w/v;
Glacial Acetic Acid 0.3% w/v;
Propylene Glycol 7.5% w/v;
Benzyl Alcohol 5% w/v; and,
Purified Water to total 100%.
pH of about 6.24.
Formulation XXXXV
Minoxidil 8% w/v;
Latanoprost 0.3% or 0.1% w/v;
Ethanol 50.0% w/v;
Polysorbate 60 0.4% w/v;
Polyoxyethylene lauryl alcohol 1% w/v;
Acetic Acid q.s. pH 6.0 w/v;
Propylene Glycol 10% w/v;
Benzyl Alcohol 5% w/v; and,
Purified Water to total 100%
Formulation XXXXVI (Lotion)
Minoxidil 5% w/v;
Latanoprost 0.1% or 0.3% w/v;
Ethanol 47.50% w/v;
Polysorbate 60 0.4% w/v;
Polyoxyethylene lauryl alcohol 1.00% w/v;
Acetic Acid q.s. pH 6.0;
Benzyl Alcohol 5% w/v; and,
Purified Water to total 100%.
Formulation XXXXVII
Minoxidil 5% w/v;
Latanoprost 0.1% w/v;
Ethanol 47% w/v;
Polysorbate 60 0.4% w/v;
Polyoxyethylene
lauryl alcohol 1% w/v;
Acetic Acid 1% w/v;
Propylene Glycol 10% w/v;
Benzyl Alcohol 5% w/v; and,
Purified Water QS 100%.
Formulation XXXXVIII
Minoxidil 5% w/v;
Latanoprost 0.3% w/v;
Ethanol 44.2% w/v;
Polysorbate 60 0.4% w/v;
Polyoxyethylene
lauryl alcohol w/v 1% w/v;
Acetic Acid 0.3% w/v;
Propylene Glycol 30% w/v;
Benzyl Alcohol 2% w/v; and,
Purified Water QS 100%.
Formulation XXXIX
Minoxidil 5% w/v;
Latanoprost 0.3% w/v;
Ethanol 46% w/v;

Polysorbate 60 0.4% w/v;
Polyoxyethylene
lauryl alcohol 1% w/v;
Acetic Acid 0.3% w/v;
Propylene Glycol 30% w/v;
Benzyl Alcohol 10% w/v; and,
Purified Water QS 100%.
Formulation XXXXX
Minoxidil sulphate 4% w/v;
Latanoprost 0.08% w/v;
Ethanol 30% w/v;
Propylene Glycol 50% w/v;
Oleyl Alcohol 2% w/v;
Transcutol 3% and,
Purified Water QS 100%.

The apparent pH of the final Formulations XXXXIV-XXXXX adjusted to 6.0-6.5 benzyl alcohol can be eliminated for single use formulations and substituted with propylene glycol.

OTHER EMBODIMENTS

Other formulations include a composition comprising up to 5% w/w minoxidil, latanoprost at about 0.1% w/w; carbomer at about 0.15% w/w; triethylamine (TEA) at about 0.22% w/w; ethanol at about 15.0% w/w; diethylene glycol monoethyl ether at about 10.0% w/w; polysorbate 20 at about 4.0% w/w; and water at about 70.5% w/w.

A composition comprising up to 5% w/w minoxidil, latanoprost at about 0.1% w/w; carbomer at about 0.10% w/w; NaOH at about 0.035% w/w; ethanol at about 15.0% w/w; diethylene glycol monoethyl ether at about 10.0% w/w; and water at about 74.8% w/w.

A composition comprising up to 5% w/w minoxidil, latanoprost at about 0.1% w/w; carbomer at about 0.125% w/w; TEA at about 0.18% w/w; ethanol at about 30.0% w/w; diethylene glycol monoethyl ether at about 20.0% w/w; and water at about 49.59% w/w.

A composition comprising up to 5% w/w minoxidil, latanoprost at about 0.1% w/w; carbomer at about 0.10% w/w; TEA at about 0.15% w/w; ethanol at about 30.0% w/w; propylene glycol at about 20% w/w; and water at about 49.7% w/w.

A composition comprising up to 5% w/w minoxidil, latanoprost at about 0.1% w/w; carbomer at about 0.20% w/w; TEA at about 0.22% w/w; ethanol at about 60.0% w/w; glycerin at about 5.0% w/w; and water at about 34.48% w/w.

A composition comprising up to 5% w/w minoxidil, latanoprost at about 0.1% w/w; carbomer at about 0.25% w/w; TEA at about 0.38% w/w; ethanol at about 60.0% w/w; polysorbate 20 at about 4.0% w/w; and water at about 35.27% w/w.

A composition or solution comprising 4% w/v minoxidil, 0.08% w/v latanoprost, 50% w/v propylene glycol, 30% w/v ethanol, 3% w/v transcutol, 2% w/v oleyl alcohol, 0.5% w/v Polyoxyethylene 40, and q.s. water 100%.

A composition or solution comprising 4% w/v minoxidil, 0.08% w/v latanoprost, 50% w/v propylene glycol, 30% w/v ethanol, 3% w/v transcutol, 2% w/v oleyl alcohol, and q.s. water 100%.

A composition comprising up to 5% w/w minoxidil, latanoprost at about 0.1% w/w; carbomer at about 0.25% w/w; TEA at about 0.38% w/w; ethanol at about 50.0% w/w; diethylene glycol monoethyl ether at about 10% w/w; polysorbate 20 at about 4.0% w/w; and water at about 35.27% w/w.

It is extremely challenging to formulate two insoluble drugs such as minoxidil and latanoprost together into a single aqueous composition. Both compounds have poor solubility in water and require high concentrations of solvents and or cosolvents to keep both compounds in solution particularly at the very high concentrations of minoxidil which is often 2-7% w/v. Further, it is noted that many consumers find the generic Rogaine® formulation unpleasant or intolerable in that it is sticky and many users perceive that it leaves a sticky or greasy residue which decreases patient compliance. This is believed to be mainly due to propylene glycol which is present at 50% w/v which is necessary to solubilize the high concentration of minoxidil, generally at 5% w/v, which is a very insoluble substance. It has been found that addition of low concentrations diethylene glycol monoethyl ether and oleyl alcohol made the solution less sticky and more pleasant to the touch and feel of the solution. It was also surprisingly found that not only did the addition of these compounds result in a better feeling formulation, the addition of these compounds, particular diethylene glycol monoethyl ether and oleyl alcohol in low concentrations, resulted in a more efficacious formulation that was superior in growing hair. Although not wishing to be bound to any theory, it is believed that the combination of diethylene glycol monoethyl ether and oleyl alcohol act synergistically at certain concentrations, increase skin penetration of the active agents (e.g., latanoprost and minoxidil) and fluidize the lipids of hair follicle and the stratum corneum and make both active agents more soluble in vivo which make the formulations more efficacious by increasing the bioavailability of the active agents. Latanoprost is mostly lipid soluble which allows it to penetrate into the hair follicles of the epidermis. However, when used in combination with certain solvents such as diethylene glycol monoethyl ether and oleyl alcohol, the formulation becomes more effective in exfoliating the pore lining, loosens clogs, removes impurities, and allows the formulation to permeate more freely. By weakening the cellular glue, so to speak, exfoliation opens up the hair follicle and pores. This would account for the increased efficacy of these formulations as compared to the same formulations that did contain diethylene glycol monoethyl ether and oleyl alcohol.

In some embodiments, the composition comprises water, minoxidil, latanoprost at a concentration of about 0.01% w/w to about 0.4% w/w, or about 0.05-0.3% w/w, or about 0.1-0.3% w/w. Minoxidil is comprised in an amount of about 0.5-10% w/w, or about 1-6% w/w, or about 2-5% w/w or about 5% w/w and one or more selected from the group consisting of: cetostearyl alcohol at a concentration of about 0.5% w/w to about 1% w/w, glyceryl mono-oleate at a concentration of about 1% w/w to about 3% w/w, preferably about 2% w/w, oleyl alcohol at a concentration of about 1% w/w to about 3% w/w, preferably about 2% w/w, ethanol at a concentration of about 30% w/w to about 75% w/w, propylene glycol at a concentration of about 10% w/w to about 25% w/w, benzyl alcohol at a concentration of about 0.5% w/w to about 2% w/w, preferably about 1% w/w, carbomer at a concentration of about 0.15% w/w, triethanolamine at a concentration of about 0.16% w/w, and glycerol at a concentration of about 0.5% w/w to about 10% w/w, preferably 2% w/w.

In some embodiments, the composition comprises water, minoxidil, latanoprost at a concentration of about 0.01-0.5% w/w, or about 0.05-4% w/w, or about 0.1-0.5% w/w. Minoxidil is comprised in an amount of about 0.5-10% w/w, or about 1-6% w/w, more or about 2-5% w/w or about 5% w/w and one or more selected from the group consisting of transcutol at a concentration of about 1% w/w to about 25% w/w, preferably about 10% w/w, propylene glycol at a concentration of about 1% w/w to about 25% w/w, glycerol monooleate at a concentration of about 1% w/w to about 3% w/w, preferably about 2% w/w, oleyl alcohol at a concentration of about 1% w/w to about 3% w/w, preferably about 2% w/w, ethanol at a concentration of about 30% w/w to about 75% w/w, propylene glycol at a concentration of about 10% w/w to about 25% w/w, benzyl alcohol at a concentration of about 0.5% w/w to about 2% w/w, preferably about 1% w/w, carbomer at a concentration of about 0.15% w/w to about 0.2% w/w, triethanolamine at a concentration of about 0.16% w/w, and glycerin at a concentration of about 0.5% w/w to about 10% w/w, preferably 2% w/w.

Some embodiments may also comprise one or more additional ingredients in addition to those specified in the paragraph above, wherein the one or more ingredients are selected from the group consisting of linoleic acid at a concentration of about 1% w/w to about 5% w/w, preferably 2% w/w, sodium lauryl sulfate at a concentration between 0.1% w/w to about 0.5% w/w, preferably 0.2% w/w, and docusate sodium at a concentration between 0.1% w/w to about 0.5% w/w, preferably 0.2% w/w.

In some embodiments, the composition comprises water, minoxidil, latanoprost or travoprost at a concentration of about 0.01-5% w/w, or about 0.05-4% w/w, or about 0.1-0.3% w/w or about 0.1% w/w, 0.2% w/w or 0.3% w/w. Minoxidil is comprised in an amount of about 0.5-10% w/w, or about 1-6% w/w, or about 2-5% w/w or about 5% w/w and one or more selected from the group consisting of: transcutol at a concentration of about 1% w/w to about 25% w/w, preferably about 10% w/w, propylene glycol at a concentration of about 1% w/w to about 25% w/w, glycerol monooleate at a concentration of about 1% w/w to about 3% w/w, preferably about 2% w/w, oleic acid at a concentration of about 1% w/w to about 3% w/w, preferably about 2% w/w, linoleic acid at a concentration of about 1% w/w to about 3% w/w, preferably about 2% w/w, ethanol at a concentration of about 30% w/w to about 75% w/w, propylene glycol at a concentration of about 10% w/w to about 25% w/w, benzyl alcohol at a concentration of about 0.5% w/w to about 2% w/w, preferably about 1% w/w, carbomer at a concentration of about 0.15% w/w to about 0.2% w/w, triethanolamine at a concentration of about 0.16% w/w, glycerin at a concentration of about 0.5% w/w to about 10% w/w, preferably about 2% w/w, essential oil at a concentration of about 0.05% w/w to about 5% w/w, preferably about 1% w/w, limonene at a concentration of about 0.5% w/w to about 5% w/w, preferably about 1% w/w, nerol at a concentration of about 0.5% w/w to about 5% w/w, preferably about 1% w/w, cineol at a concentration of about 0.5% w/w to about 5% w/w, preferably about 1% w/w, octyl salicylate at a concentration of about 0.5% w/w to about 5% w/w, preferably about 2% w/w, DMSO at a concentration of about 0.5% w/w to about 5% w/w, preferably about 2% w/w, DDAB at a concentration of about 0.01% w/w to about 1% w/w, preferably about 0.2% w/w, sodium taurodeoxycholate at a concentration of about 0.01% w/w to about 5% w/w, preferably about 2% w/w, docusate sodium at a concentration of about 0.01% w/w to about 1% w/w, preferably about 0.2% w/w, myristyl myristate at a concentration of about 1% w/w to about 30% w/w, preferably about 25% w/w, polysorbate 80 at a concentration of about 1% w/w to about 5% w/w, preferably about 2% w/w, silicone elastomer in cyclomethicone at a concentration of about 40% w/w to about 80% w/w, preferably about 73.5% w/w, Dow Silky Wax 10 at a concentration of about 1% w/w to about 20% w/w, preferably about 8% w/w, isopropyl myristate at a concentration of about 1% w/w to about 20% w/w, preferably about 8% w/w.

In some embodiments, the composition comprises water; minoxidil or finasteride, latanoprost or travoprost, for example with latanoprost or topical finasteride at a concentration from about 0.01% w/w to about 0.5% w/w, preferably about 0.05-0.45% w/w or about 0.075-0.4% w/w, more preferably about 0.1-0.3% w/w the most preferred value being 0.1% w/w, 0.2% w/w or 0.3% w/w. Minoxidil or finasteride comprised in an amount of about 0.5-10% w/w, or about 1-6% w/w, or about 2-5% w/w or about 5% w/w; and one or more selected from the following: ethanol, for example at a concentration between 0.01% w/w to about 89% w/w; propylene glycol, for example at a concentration between 0.01% w/w to about 89% w/w; diethylene glycol monoethyl ether, for example at a concentration between 0.01% w/w to about 89% w/w; benzyl alcohol, for example at a concentration between 0.01% w/w to about 89% w/w; and one or more fatty acids and/or fatty ester excipients, for example at a concentration between 0.01% w/w to about 10% w/w. In some embodiments, the fatty acids may include one or more C8-mC28 fatty acids, and which may be saturated, monounsaturated, or polyunsaturated. In some embodiments, a saturated fatty acid may be stearic acid. In some embodiments, a monounsaturated fatty acid may be oleic acid. In some embodiments, a polyunsaturated fatty acid may be linoleic acid. In some embodiments, the fatty ester may one or more include C8-C28 fatty acids, and which may be saturated, monounsaturated, or polyunsaturated. In some embodiments, a saturated fatty ester may be glyceryl monostearate. In some embodiments, a monounsaturated fatty ester may be glyceryl monooleate. In some embodiments, a polyunsaturated fatty ester may be ethyl ester of linoleic acid.

A preferred composition comprises minoxidil or finasteride, latanoprost or travoprost, oleyl alcohol, ethanol and propylene glycol. Latanoprost or travoprost is comprised in an amount of about 0.01-0.5% w/w, or about 0.05-0.4% w/w, or about 0.1-0.3% w/w the most preferred or about 0.1% w/w, 0.2% w/w or 0.3% w/w. Minoxidil or finasteride is comprised in an amount of about 0.5-10% w/w, or about 1-6% w/w, or about 2-5% w/w or about 5% w/w. Oleyl alcohol is comprised in an amount of about 1-10% w/w. Ethanol is comprised in an amount of about 50-80% w/w. Propylene glycol is comprised in an amount of 15-15% w/w.

Examples of particularly preferred compositions for growing hair by topical application comprise minoxidil or finasteride, latanoprost or travoprost in free form or a pharmaceutically acceptable salt thereof, wherein the latanoprost or travoprost is contained in an amount of about 0.1% w/w to about 4% w/w; minoxidil or finasteride is comprised in an amount of about 0.5-10% w/w, preferably about 1-6% w/w, more preferably about 2-5% w/w the most preferred value being 5% w/w.; at least one first compound selected from a fatty acid, fatty acid alcohol and fatty ester, wherein said composition is formulated for topical administration to the skin.

In some embodiments, the first compound is a fatty acid. The fatty acid may be saturated or unsaturated. In some embodiments, the fatty acid is selected from the group consisting of stearic acid, oleic acid, linoleic acid, and mixtures thereof. In some embodiments, the first compound is a fatty ester. The fatty ester may be saturated or unsaturated. The fatty ester may be selected from the group consisting of glyceryl monostearate, glyceryl monooleate, and ethyl ester of linoleic acid. In some embodiments, the composition comprises at least two first compounds. The composition may comprise a mixture of at least one fatty acid and at least one fatty ester. The first compound may have 12-24 carbon atoms. The composition may further comprise at least one second compound selected from the group consisting of ethanol, propylene glycol, diethylene glycol monoethyl ether, and benzyl alcohol. The composition may further comprise at least one third compound selected from the group consisting of terpenes, occlusive agents, surface active agents, sulfoxides, cyclic ethers, amides, amines, and dimethylaminopropionic acid derivatives. In some embodiments, the terpene is selected from the group consisting of terpinolene, limonene, nerol, and cineol. In some embodiments, the occlusive agent is selected from the group consisting of silicones, mineral oils, and water insoluble polymers. In some embodiments, the surface active agent is selected from the group consisting of polysorbate 20, polysorbate 40, polysorbate 60, polysorbate 80, sodium dodecyl sulfate, sodium lauryl sulfate, DMSO, and docusate sodium. In some embodiments, the dimethylaminopropionic acid derivative is 2-dimethylaminopropionic acid dodecyl ester. The composition may comprise latanoprost in an amount of about 0.01% w/w to about 4% w/w. More preferably, the composition may comprise latanoprost in an amount of about 0.05% w/w to about 0.5% w/w. Most preferably, the composition may comprise latanoprost in an amount of about 0.1% w/w. In some embodiments minoxidil is comprised in an amount of about 0.5-10% w/w, preferably about 1-6% w/w, more preferably about 2-5% w/w the most preferred value being 5% w/w. the composition is in the form of one selected from the group consisting of solutions, gels, ointments, foams, films, liniments, creams, shampoos, lotions, pastes, jellies, sprays and aerosols. In some embodiments, the composition is packaged in a kit with an applicator for application to the skin.

The compositions and formulations of the present invention can be manufactured using the following general procedure:

Non-aqueous components (e.g. latanoprost, travoprost, minoxidil, finasteride ethanol, glycols) are combined in a beaker and stirred using a propeller type overhead mixer until the solution is clear. Water is added to the non-aqueous mixture followed by the addition of the thickening agent. Upon dispersion of the thickening agent, a base is added to neutralize the polymer and thicken the solution into a gel other desired composition. For example, ethanol, minoxidil and latanoprost are combined in a beaker and stirred using a propeller type overhead mixer until the solution is clear. This mixture is then added to the non-aqueous ingredients to form a non-aqueous mixture. In a separate vessel the thickening agent is dispersed in water to form an aqueous mixture, which is then added to the non-aqueous mixture. Upon mixing of the non-aqueous and aqueous mixtures, a base is added to neutralize the polymer and to thicken the solution into a gel.

The compositions of the present invention can be manufactured using the following general procedure:

Ethyl alcohol is weighed into a suitable media jar equipped for mixing, bimatoprost, latanoprost or travoprost is then added to the ethyl alcohol and stirred at moderate speed until dissolved. Into separate mixing tank, minoxidil, diethylene glycol monoethyl ether, oleyl alcohol, propylene glycol and optionally POE 40 are added and mixed until the solvents are dispersed. Ethyl alcohol/(bimatoprost, latanoprost, or travoprost) solution is then added into the non-aqueous solution and mixed until the components are homogenously mixed (about 5 minutes of mixing). If a gel is desired, to the above mixture the carbomer thickener previously dispersed in water is added and mixed until well dispersed, once dispersed a base is added to thicken the solution into a gel.

A topical 0.0.5% w/w latanoprost/5% w/w minoxidil cream is prepared as follows: Medium viscosity carboxymethyl cellulose and spermaceti are melted together at a temperature of 70-80° C. Propylene glycol, polysorbate 80, latanoprost, minoxidil and transcutol are added in turn, maintaining a temperature of 75-80° C. A preservative (e.g., methylparaben) is added slowly to the carboxymethyl cellulose and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Once formulated, the formulations may be applied continuously daily, monthly or yearly.

Example I

A 42-year old Caucasian man with alopecia areata applies the formulation of Formulation VIII twice a day, 2 ml/day to areas on his scalp where hair loss is evident, presenting as small patches of hair loss approximately the size of a quarter. After thirty days of application, there will be fewer T cell infiltrates in the patient's scalp hair follicles and the patient's hair will begin to grow on the patches.

Example II

A 32-year old male with androgenetic alopecia applies the formulation of Formula VI to areas of hair loss on his scalp at least once a day (1 ml/day). After forty-five days of continuous application, the underlying autoimmune response causing hair loss will lessen in severity and hair will begin to regrow on the patient's scalp in the areas of hair loss.

Example III

A 43-year old female suffering from telogen effluvium applies the formulation of Formula XVII to her scalp twice a day. After thirty-five days of daily application, the patient's hair will begin to regrow on the patient's scalp in areas where the patient suffered hair loss. The patient will experience no side effects from application of Formulation XVII to the scalp.

Example IV

A 62 year old woman with thinning eyebrows applies Formulation XXII to her eyebrows with an applicator once a day. Within 45-90 days, the patient will experience increased growth of eyebrow hairs which are longer, thicker and darker than eyebrow hairs had she not have applied Formulation XXII.

Example V

A 53-year old male shaved an approximately one inch by one inch area the underside of his left and right forearm. All hair above the epidermis was removed. The patient applied approximately 0.5 ml of Formulation XI once each day to the left forearm but left the right forearm untreated. After 20 days, the hairs on the left forearm were more numerous, longer, darker and thicker as compared to the hairs on the right forearm which were less numerous, shorter, lighter and not as thick. After 30 days, the hairs on the left forearm were more numerous, longer, darker and thicker as compared to the hairs on the right forearm which were less numerous, shorter, lighter and not as thick. The patient experienced no side effects.

Example VI

A 53-year old male shaved a four inch by two-inch area above his left and right knee to remove all hair above the epidermis and applied the formulation of Formula XI to the shaved area above the left knee once a day and 5% minoxidil generic ROGAINE® solution above the right knee once a day. After twenty days the hair growth in the area shaved above the left knee is slightly greater (more hair, longer hair and thicker) than in the area shaved above the right knee. After 30 days the hair in the area above the left knee is longer, darker and thicker than the area above the right knee. After 45 days, the hair above the left knee is significantly longer, thicker in diameter, darker and more numerous than the area above the left knee which was treated with a 5% minoxidil Rogaine® solution. The patient suffered no side effects.

Example VII

A 54 year old Caucasian male shaved three one-inch-by-one inch square areas (Areas #1-#3) on his thigh, two side by side and one below. All hair above the epidermis was removed. Areas #1 and #2 were treated and Area #3 received no formulation and served as a control. The patient applied about one-third ml of Formulation XX per day to Area #1 and one-third milliliter of Formulation XVIII to Area #2. Area #3 received no treatment and served as a control. After 30 days, both Areas 1 and 2 had significant hair growth, the hairs were longer, darker and thicker as compared to the control (Area #3). There did not appear to be a significant difference between Area #1 and Area #2 in regard to length of hair or darkness or thickness after 30 days. However, Area #1 and Area #2 had significantly more hair growth than Area #3. After 60 days, both Areas #1 and #2 had significant hair growth but the difference between the two areas in regard to length, thickness and darkness was not significant with Area #1 having about 10% more and longer hair than Area #2.

In regard to darkness and thickness, there appeared to be no significant difference between Areas #1 and #2.

Example VIII

Figure 5:
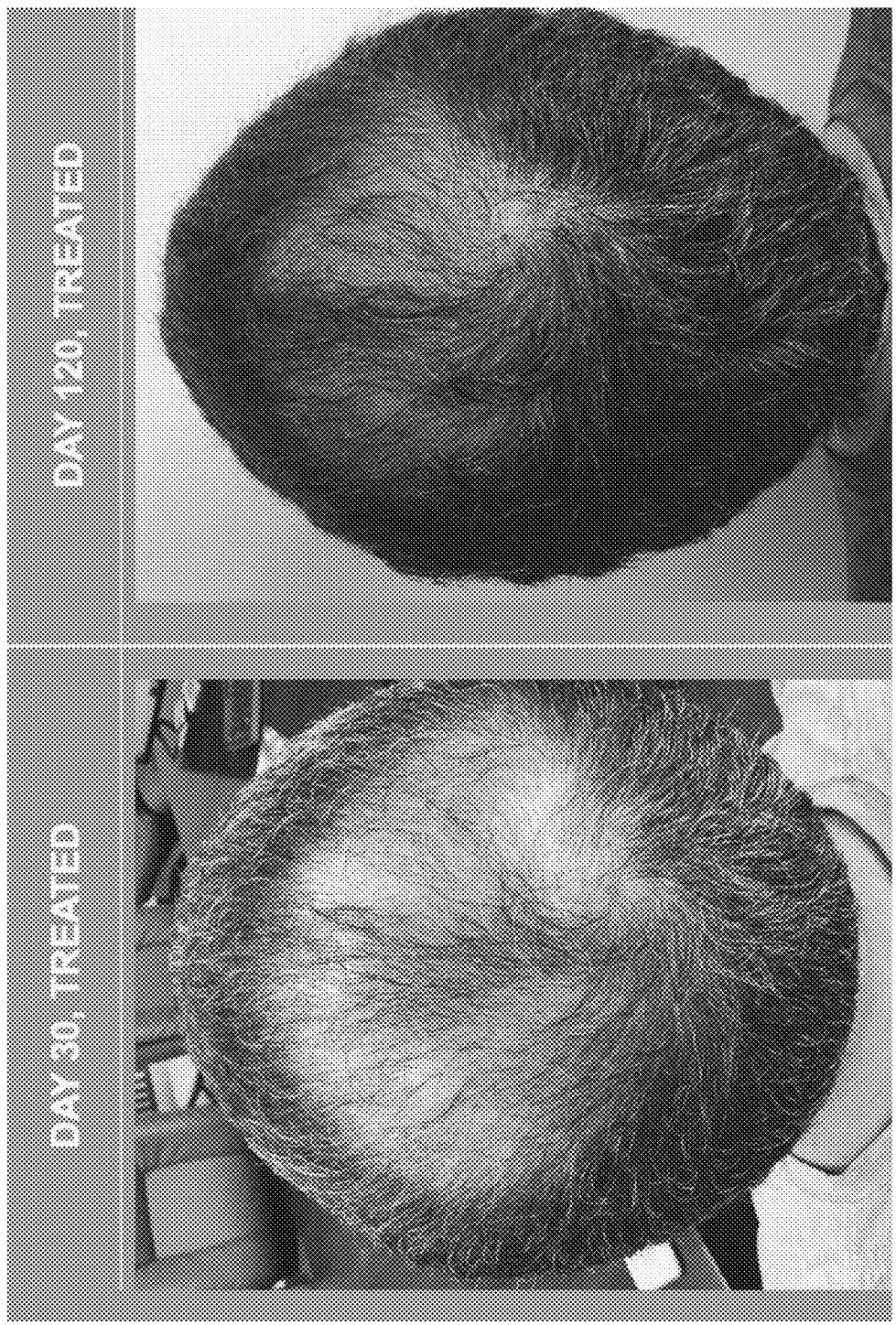

A Caucasian male, age 53, with balding on his crown roughly corresponding to stage IV on the Hamilton Norwood Scale, applied Formulation XX once a day, at approximately 1 ml/day to his crown and the front of his head. At Day 75, the patient switched to Formulation XVIII. After 90 days, the patient experienced significant regrowth to his crown with approximately 40-50% of the balding area being reduced in area with new hair growth (see FIG. 5). Most of the new hair growth was with darker hair of the patient's natural hair color and the overall ratio of dark hair to grey hair increased significantly in the treated area. The new hair was longer, darker and thicker as compared to the vellus hair in the balding area of his crown. The patient also experienced significant regrowth in the front of his head where formulation was applied. The patient experienced no side effects.

Example IX

A 54 year old male shaved three areas of his thigh above his knee in approximately two inch by three inch areas where the hair was closely shaved down to the surface of the epidermis. Two areas on the left thigh separated by several inches in distance and an area on his right thigh. The subject applied no formulation to Area #1 and left that area untreated, applied a generic 5% minoxidil Rogaine® solution to Area #2 at approximately 0.3 ml/day, and applied a minoxidil/latanoprost formulation (Formulation XVIII) to Area #3 at approximately 0.3 ml/day. After approximately 15 days, the untreated area showed some hair growth while Area #2 and Area #3 experienced more pronounced hair growth as compared to Area #1. Area #2 and Area #3 were very similar in numbers and lengths of hairs but the hairs of Area #3 appeared slightly darker and thicker. At Day 30, all three areas experienced regrowth with Areas #2 and #3 having significantly greater numbers of hair, which were longer, darker and with greater diameter as compared to Area #1. At Day 30, the number of hairs in Areas #2 and #3 were roughly the same but the hairs of Area #3 appeared slightly darker and thicker than Area #2. At Day 45, Area 1 had regrowth, approximately half of the hairs were regrown but was significantly less than Areas #2 and #3. At Day 45, Area #3 had significantly more hairs than Area #2, with greater length, darkness and thickness as compared to Area #2.

Example X

A 54 year old male patient shaved three areas (approximately one inch by one inch) on his thigh so all of the hair was removed from those areas above the dermis. Once a day, the patient begins applying Formulation XXXV on Area #1, then an identical formulation but without latanoprost (4% w/v minoxidil solution) to Area #2, and an identical formulation to Formulation XXXV but without minoxidil (0.08% w/v latanoprost solution) to Area #3. After fifteen days, Area #1 had earlier onset of hair growth and experienced greater regrowth and an earlier onset of hair as compared to areas #2 and #3 in that there were more hairs growing above the epidermis, with greater thickness and greater darkness than areas #2 and #3. There was little to no difference between the hair growth in terms of numbers of hair, length of hair, thickness of hair or darkness of hair between areas #2 and #3 on Day 15. By Day 30, area #1 had more regrowth as compared to areas #2 and #3 with more hair, longer hairs, thicker hairs and darker hairs compared to area #3. Area #1 had a quicker onset of hair growth and greater hair growth as compared to areas #2 and #3. The patient experienced no side effects.

Example XI

Figure 4:
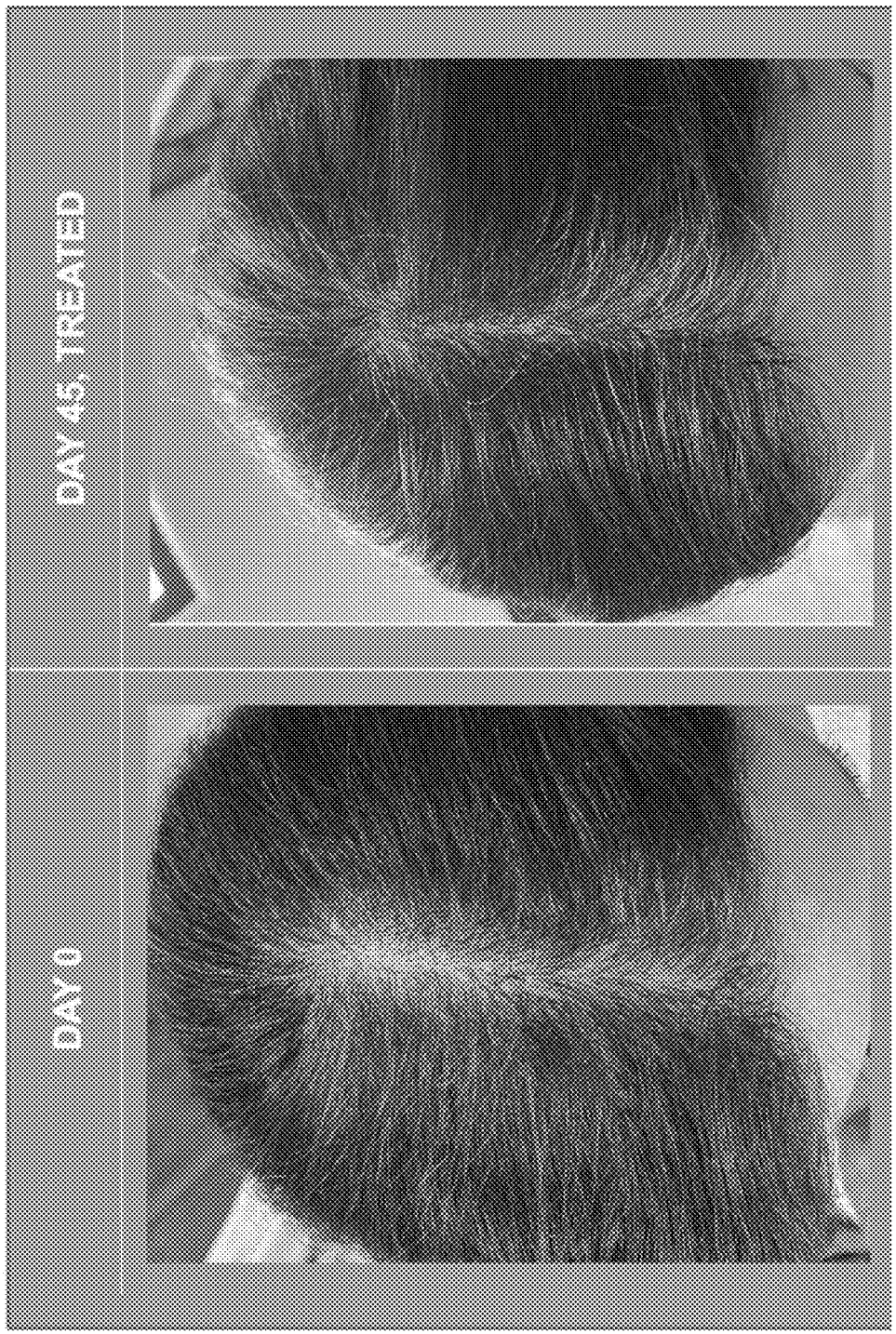
FIG. 4 shows hair growth on a 46 year old female patient applying Formulation XX followed by Formulation XVIII; and, FIG. 5 shows hair growth on a 53 year old male patient applying Formulation XX followed by Formulation XVIII.

A Caucasian female, age 46, with balding and thinning hair along her vertex corresponding to stage I on the Ludwig scale, applied Formulation XX on her head along her vertex twice a day with about 2 ml/day being applied for approximately 30 days. At approximately Day 31, the patient began to apply Formulation XVI once a day (1 ml/day) to her head along her vertex. By Day 45, the patient's vertex had filled in significantly with new hair growth that was of her original hair color wherein the ratio of dark hair to grey hair increased considerably with more dark hair of her original hair color as compared to grey hair (see FIG. 4). The individual hairs of the new hair growth were also thicker as compared to her existing hairs. The patient experienced no side effects.

Example XII

A 54 year old patient shaved three areas (approximately one inch by one inch) on his arm so all of the hair was removed from above the surface of the epidermis. Once a day, the patient applied Formulation XVIII on area #1, an identical solution to Formulation XVIII but without the latanoprost on area #2 and an identical solution to Formulation XVIII but without the minoxidil on area #3. After fifteen days, area #1 had earlier onset of hair growth and more hair growth (more hair growing above the epidermis, longer, darker and thicker) than areas #2 and area #3. By Day 30, the trend continued with area #1 experiencing significant regrowth as compared to area #2 and area #3. By Day 45, the area #1 had almost completely grown back as compared to either area #2 or area #3. Area #3 had slightly darker and thicker hair as compared to area #2 but area #2 growth was slightly longer than area #3. However, area #1 had more growth with longer, darker and thicker hair than area #3 and longer hair than area #2.

Example XIII

A 54 year old patient removed hair by shaving three areas (approximately 1 inch by one inch) on his upper thigh so all of the hair was removed from these areas. Once a day, the patient applied Formulation XVIII on Area #1, Formulation XXXV on area #2 and no formulation on Area #3. After fifteen days, both Area #1 and Area #2 experienced significant regrowth as compared to area #3. The hairs in Areas #1 and #2 were longer, darker, thicker and more numerous as compared to Area #3. By Day 30, both Areas #1 and #2 had significant regrowth as compared to Area #3 with more hair, longer hairs, thicker hairs and darker hairs compared to area #3. By Day 45, the Areas #1 and #2 were both almost completely grown back and area #3 had significantly less hair growth than either Areas #1 or #2.

There was no significant difference in hair growth between Areas #1 and #2. The patient experienced no side effects.

Example XIV

A 54 year old patient removed hair by shaving three areas (approximately 1 inch by one inch), two on his right calf and one on his left calf so all of the hair was removed above the epidermis in these areas. Once a day, the patient applied Formulation XVIII on Area #1, an area on his left calf, no formulation on Area #2 on his less calf and Formulation XIX on Area #3. After fifteen days, both Area #1 and Area #3 experienced significant regrowth as compared to Area #2 with Area #3 having more hair growth (more hair, longer, and thicker) than Area #2. By Day 30, both Areas #1 and #3 had significant regrowth as compared to Area #2 with more hair, longer hairs, thicker hairs and darker hairs compared to Area #3. By Day 30, Area #3 had significantly more hair growth with more numerous, longer, and darker hair than Area #2 by approximately 20%. The patient experienced no side effects.

Example XV

A 62 year old Caucasian female had thinning hair along her vertex. The patient began applying Formulation XX twice a day, approximately 2 mls a day, by spraying 1 ml a day along the vertex, twice a day. At Day 27, the patient switched to Formulation XVIII applied once a day, by spraying approximately 1 ml of formulation on her vertex each day. The patient sprayed Formulation XVIII for 30 days.

At Day 73, the patient's hair had significantly grown back along the vertex, with thicker and fuller hair with hair growth on the crown, but not yet completely filled in.

Example XVI

A 59 year old Caucasian female with thinning hair long her vertex, began applying Formulation XX twice a day, approximately 2 ms a day, by spraying 1 ml a day onto the area of the scalp losing hair, twice a day. After 31 days, the patient switched to Formulation XVIII applied once a day, by spraying approximately 1 ml of formulation each day. The patient sprayed Formulation XVIII for 78 days. At Day 108, the patient's hair had significantly regrown along the vertex.

Example XVII

A 64 year old Caucasian female with hair loss along her forehead and temples began applying Formulation XX twice a day, approximately 2 ms a day, by spraying 1 ml a day onto the area of the scalp losing hair, twice a day. On Day 30, the patient switched to Formulation XVIII applied once a day, by spraying approximately 1 ml of formulation each day. By Day 106, the patient experienced significant new hair growth along her forehead and temples with hair that was darker and thicker than the existing hair that was in those areas prior to treatment.

Example XVIII

A 26 year old Caucasian male with slight balding on his crown, began applying Formulation XX twice a day, approximately 2 ms a day, by spraying 1 ml a day onto the area of the scalp losing hair, twice a day. On Day 29, the patient switched to Formulation XVIII applied once a day, by spraying approximately 1 ml of formulation each day. On Day 99, the patient experienced increased hair growth on his crown and the balding area was less visible.

Example XIX

A 44 year old Caucasian male had significant balding on his crown corresponding roughly to a Norwood-Hamilton score of IV. The patient began applying Formulation XX twice a day, approximately 2 ms a day, by spraying 1 ml a day onto the area of the scalp losing hair, twice a day. On Day 29, the patient switched to Formulation XVIII applied once a day, by spraying approximately 1 ml of formulation each day. On Day 118, the patient's hair had significantly grown back on the crown, with the hair darker and thicker than the hair in the same area prior to treatment. By Day 108, about half of the crown was grown in with terminal hair where either no hair or vellus hair previously existed.

Example XX

A 59 year old female patient with thinning along her vertex corresponding to roughly an I-2 or I-3 on the Ludwig Scale, began applying Formulation XX twice a day, approximately 2 mls a day, by spraying 1 ml a day onto the area of the scalp losing hair, twice a day. On Day 30, the patient switched to Formulation XX twice a day, approximately 2 mls a day, by spraying 1 ml a day onto the area of the scalp losing hair, twice a day. On Day 99, the vertex was thicker and fuller with much of the vertex covered with new hair which was thicker than the hair in the same area prior to treatment.

The invention claimed is:

1. A composition for use in the treatment of hair loss wherein the active agents consist of about 0.05%-0.5% w/v latanoprost and 0.01%-0.1% w/v cyclosporine.

2. The composition of claim 1 further comprising oleyl alcohol or ethanol.

3. The composition of claim 2 further comprising one selected from the group consisting of polyethylene glycol or propylene glycol.

4. The composition of claim 3 further comprising acetic acid and one selected from the group consisting of polysorbate 60 and polyoxyethylene lauryl alcohol.

5. The composition of claim 3 further comprising acetic acid one selected from the group consisting of polysorbate 60 and polyoxyethylene lauryl alcohol.

6. The composition of claim 2 further comprising ethanol and at least one selected form the group consisting of propylene glycol and polysorbate 80.

7. The composition of claim 2 wherein ethanol is present in a concentration of about 25%-30% w/v.

8. The composition of claim 3 wherein the composition further comprises oleyl alcohol.

9. The composition of claim 3 further comprising diethylene glycol monoethyl ether.

10. The composition for use in hair loss wherein the active agents consist of about 0.05-0.3% w/v latanoprost and 0.01%-0.1% w/v cyclosporine.

11. The composition of claim 10 further comprising ethanol, propylene glycol, water and at least one selected from the group consisting of benzyl alcohol, oleic acid and polyoxyethylene lauryl alcohol.

12. The composition of claim 10 wherein the composition comprises ethanol, propylene glycol, polysorbate, water and at least one selected from the group consisting of oleyl alcohol, oleic acid and benzyl alcohol.

13. The composition of claim 12 wherein the composition comprises propylene glycol, ethanol and acetic acid and wherein acetic acid is present from about 0.1-0.5% w/v.

14. The composition of claim 3 wherein the composition comprises 50% w/v propylene glycol and 30% w/v ethanol.

15. The composition of claim 10 wherein the composition comprises at least two selected from the group consisting ethanol, propylene glycol, polyoxyethylene 80, and propanediol and at least one selected from the group consisting of acetic acid, oleic acid and oleyl alcohol.

16. The composition according to claim 10 further comprising about 0.1% w/v latanoprost and about 0.1% w/v cyclosporine.

17. The composition according to claim 16 further comprising propylene glycol, ethanol, and diethylene glycol monoethyl ether.

18. A composition according to claim 17 wherein the composition comprises 50% w/v propylene glycol, 25% w/v ethanol, 2-5% w/v diethylene glycol monoethyl ether and water.

19. A composition according to claim 10 consisting of 0.3% w/v latanoprost, 0.1% w/v cyclosporine, 3% w/v oleic acid, 50% w/v propylene glycol, 30% w/v ethanol, water and 3% w/v diethylene glycol monoethyl ether.

20. A composition according to claim 10 consisting of 0.1% w/v latanoprost, 0.1% w/v cyclosporine, 3% w/v oleic acid, 50% w/v propylene glycol, 30% w/v ethanol, water and 2% w/v diethylene glycol monoethyl ether.

* * * * *